(12) United States Patent
Warren et al.

(10) Patent No.: US 9,416,080 B2
(45) Date of Patent: Aug. 16, 2016

(54) CATALYTIC C—H BOND ACTIVATION

(71) Applicant: Georgetown University, Washington, DC (US)

(72) Inventors: Timothy H. Warren, McLean, VA (US); Nicholas G. Sapiezynski, Alexandria, VA (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 14/405,663

(22) PCT Filed: Jun. 14, 2013

(86) PCT No.: PCT/US2013/045903
§ 371 (c)(1),
(2) Date: Dec. 4, 2014

(87) PCT Pub. No.: WO2013/188771
PCT Pub. Date: Dec. 19, 2013

(65) Prior Publication Data
US 2015/0321982 A1    Nov. 12, 2015

Related U.S. Application Data

(60) Provisional application No. 61/812,963, filed on Apr. 17, 2013, provisional application No. 61/660,349, filed on Jun. 15, 2012.

(51) Int. Cl.
| | |
|---|---|
| *C07C 43/02* | (2006.01) |
| *C07C 43/16* | (2006.01) |
| *C07C 41/01* | (2006.01) |
| *C07F 1/08* | (2006.01) |
| *C07C 319/14* | (2006.01) |
| *C07C 41/05* | (2006.01) |
| *C07D 213/70* | (2006.01) |
| *C07D 263/12* | (2006.01) |
| *C07D 263/52* | (2006.01) |
| *C07C 321/14* | (2006.01) |
| *C07C 321/16* | (2006.01) |

(52) U.S. Cl.
CPC ............... *C07C 41/05* (2013.01); *C07C 41/01* (2013.01); *C07C 319/14* (2013.01); *C07D 213/70* (2013.01); *C07D 263/12* (2013.01); *C07D 263/52* (2013.01); *C07C 2101/14* (2013.01); *C07C 2101/16* (2013.01)

(58) Field of Classification Search
CPC .......... C07F 1/08; C07C 43/02; C07C 43/16; C07C 41/01; C07C 319/14; C07C 321/14; C07C 321/16
USPC ..................... 568/38, 579; 556/110
See application file for complete search history.

(56) References Cited

U.S. PATENT DOCUMENTS 8,471,051 B2 * 6/2013 Warren ............... B01J 31/1805
548/954

FOREIGN PATENT DOCUMENTS

| WO | WO-2007/123910 A2 | 11/2007 |
|---|---|---|
| WO | WO-2010/028159 A2 | 3/2010 |

OTHER PUBLICATIONS

Sun, X. et al., "A facile synthesis of 3,5-dimethyl-4-hydroxybenzaldehyde via copper-mediated selective oxidation of 2,4,6-trimethylphenol", *Catalysis Today*, 131:423-426 (Elsevier, 2008).
International Search Report and Written Opinion from PCT/US2013/045903 dated Dec. 2, 2013.

\* cited by examiner

*Primary Examiner* — Venkataraman Balasubramanian
(74) *Attorney, Agent, or Firm* — Dana M. Gordon; Foley Hoag LLP

(57) ABSTRACT

Disclosed is a method for the transition metal-mediated oxidation of C—H bonds to form C—O or C—S bonds. The methods are useful for the formation of ethers (R—OR') from alcohols, R'OH, and $sp^3$-hybridized C—H bonds in substrates, R—H. Aryl or heteroaryl acetates may also be used for C—H to C—OAr bond formation. The methods are also useful in the preparation of C—S bonds from acetyl-protected thiols, MeC(O)SR, and disulfides, RSSR. Advantageously, the methods minimize reaction steps, the handling of oxidized intermediates, and environmental impact.

22 Claims, 12 Drawing Sheets

$$\text{R-H + R'OH} \xrightarrow[\text{RT to 90 °C}]{\substack{^t\text{BuOO}^t\text{Bu} \\ 1-10 \text{ mol\%} \\ [\text{Cl}_2\text{NN}]\text{Cu} \\ -2 \text{ HO}^t\text{Bu}}} \text{R-OR'}$$

| Entry | Alcohol R'OH | C-H Substrate R-H | Product R-O-R' | [Cl₂NN]Cu Catalyst Loading | Equiv. R-H | Tp (°C) | Time (h) | R-O-R' NMR yield |
|---|---|---|---|---|---|---|---|---|
| 1 | pentanol | ethylbenzene | 1-phenylethyl pentyl ether | 1 mol% | Ca. 100 | 90 | 24 | 84% |
| 2 | pentanol | cyclohexane | cyclohexyl pentyl ether | 1 mol% | Ca. 100 | 90 | 24 | 80% |
| 3 | cyclohexanol | ethylbenzene | 1-phenylethyl cyclohexyl ether | 1 mol% | Ca. 100 | 90 | 24 | 68% |
| 4 | pentanol | ethylbenzene | 1-phenylethyl pentyl ether | 1 mol% | 10 | 90 | 24 | 48% |
| 5 | pentanol | cyclohexane | cyclohexyl pentyl ether | 1 mol% | 10 | 90 | 24 | 40% |
| 6 | pentanol | toluene | benzyl pentyl ether | 1 mol% | 10 | 90 | 24 | 20% |

Figure 4 (continued)

| Entry | Alcohol R'OH | C-H Substrate R-H | Product R-O-R' | [Cl₂NN]Cu Catalyst Loading | Equiv. R-H | Tp (°C) | Time (h) | R-O-R' NMR yield |
|---|---|---|---|---|---|---|---|---|
| 7 | cyclohexanol | ethylbenzene | 1-phenylethyl cyclohexyl ether | 1 mol% | 10 | 90 | 24 | 32% |
| 8 | pentanol | cyclohexane | pentyl cyclohexyl ether | 10 mol% | 10 | RT | 24 | 44% |
| 9 | pentanol | cyclohexane | pentyl cyclohexyl ether | 5 mol% | 10 | RT | 24 | 25% |
| 10 | pentanol | ethylbenzene | 1-phenylethyl pentyl ether | 10 mol% | 10 | RT | 48 | 38% |
| 11 | pentanol | cyclohexane | pentyl cyclohexyl ether | 1 mol% | 10 | 100 | 24 | 50% |
| 12 | pentanol | cyclohexane | pentyl cyclohex-2-enyl ether | 1 mol% | 10 | 50 | 24 | 16% |

Reaction scheme:
R-H + R'OH → R-OR' 
(ᵗBuOOᵗBu, 1–10 mol% [Cl₂NN]Cu, RT to 90 °C, −2 HOᵗBu)

| Entry | Substrate MeC(O)OR' | C-H Substrate | Product R-O-R' | [Cl₂NN]Cu Catalyst Loading | Equiv. R-H | Tp (°C) | Time (h) | R-O-R' NMR yield |
|---|---|---|---|---|---|---|---|---|
| 1 | PhOAc | cyclohexane | Cy-O-Ph | 2.5 mol% | 10 | RT | 24 | 96% |
| 2 | PhOAc | cyclohexane | Cy-O-Ph | 5 mol% | 10 | RT | 24 | 85% |
| 3 | PhOAc | cyclohexane | Cy-O-Ph | 10 mol% | 10 | RT | 24 | 89% |
| 4 | PhOAc | cyclohexane | Cy-O-Ph | 5 mol% | 5 | RT | 24 | 88% |
| 5 | PhOAc | cyclohexane | Cy-O-Ph | 10 mol% | 5 | RT | 24 | 91% |
| 6 | PhOAc | ethylbenzene | PhCH(Me)OPh | 1 mol% | 10 | 90 | 24 | 65% |

Figure 5 (continued)

Reaction scheme:
R-H + R'XAc → R-XR'
Conditions: tBuOOtBu, 1-10 mol% [Cl₂NN]Cu, RT to 90 °C, −HOtBu, −AcOtBu
X = O or S

| Entry | Substrate MeC(O)XR' | C-H Substrate | Product R-X-R' | [Cl₂NN]Cu Catalyst Loading | Equiv. R-H | $T_p$ (°C) | Time (h) | R-O-R' NMR yield |
|---|---|---|---|---|---|---|---|---|
| 7 | PhOAc | cyclohexane | Ph-O-cyclohexyl | 5 mol% | 10 | 100 | 24 | 40% |
| 8 | PhOAc | cyclohexane | Ph-O-cyclohexyl | 5 mol% | 10 | 50 | 24 | 36% |
| 9 | F₃C-C(O)-OPh | ethylbenzene | PhO-CH(CH₃)Ph | 2.5 mol% | 10 | RT | 24 | 7% |
| 10 | F₃C-C(O)-OPh | cyclohexane | Ph-O-cyclohexyl | 2.5 mol% | 10 | RT | 24 | 12% |
| 11 | PhSAc | ethylbenzene | PhS-CH(CH₃)Ph | 2.5 mol% | 10 | RT | 24 | 38% |
| 12 | PhSAc | cyclohexane | Ph-S-cyclohexyl | 2.5 mol% | 10 | RT | 24 | 20% |

Figure 11

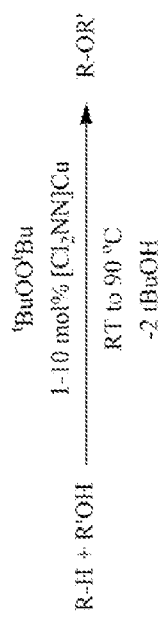

| Entry | Alcohol R'OH | C-H substrate R-H | Product R-O-R' | [Cl₂NN]Cu Catalyst Loading | Equiv. R-H | Tp (°C) | Time (h) | R-O-R' NMR Yield |
|---|---|---|---|---|---|---|---|---|
| A | CH₃OH | (ethylbenzene) | (PhCH(CH₃)OCH₃) | 1 mol% | 10 | 90 | 24 | 35% |
| B | CH₃OH | (cyclohexane) | (CyOCH₃) | 1 mol% | 10 | 90 | 24 | 44% |
| C | (cyclohexanol) | (cyclohexane) | (Cy-O-Cy) | 1 mol% | 10 | 90 | 24 | 37% |
| D | (n-octanol) | (ethylbenzene) | (PhCH(CH₃)O-octyl) | 1 mol% | 10 | 90 | 24 | 52% |
| E | (n-octanol) | (cyclohexane) | (Cy-O-octyl) | 1 mol% | 10 | 90 | 24 | 42% |
| F | ᵗBuOH (formed in situ from ᵗBuOOᵗBu) | (ethylbenzene) | (PhCH(CH₃)OᵗBu) | 5 mol% | 100 | 90 | 24 | 62% |

| Entry | Alcohol R'XAc | C-H substrate R-H | Product R-X-R' | [Cl₂NN]Cu Catalyst Loading | Equiv. R-H | Tp (°C) | Time (h) | R-O-R' NMR Yield |
|---|---|---|---|---|---|---|---|---|
| G | | | | 1 mol% | 10 | 90 | 24 | 68% |
| H | | | | 2.5 mol% | 10 | 90 | 24 | 65% |

CATALYTIC C—H BOND ACTIVATION

RELATED APPLICATIONS

This application is the U.S. national phase of International Patent Application No. PCT/US2013/045903, filed Jun. 14, 2013; which claims the benefit of priority to U.S. Provisional Patent Application Ser. No. 61/660,349, filed Jun. 15, 2012; and U.S. Provisional Patent Application Ser. No. 61/812,963, filed Apr. 17, 2013.

BACKGROUND

A number of catalytic systems can oxidize $sp^3$-hybridized C—H bonds in R—H to alcohols, R—OH. In particular, tertiary C—H bonds may be selectively oxidized to alcohols, R—OH, because the oxidized carbon in the product is stable against further oxidation. However, attempted hydroxylations of secondary C—H bonds in R—$CH_2$—R' often result in the formation of the corresponding ketone, R—C(O)—R', due to the greater ease of oxidation of the immediately resulting secondary alcohol, R—CH(OH)—R'.

Notwithstanding the work on catalytic C—H oxidation to form alcohols, there is little precedent for direct catalytic conversion of R—H to an ether, R—OR', by reaction with an alcohol, R'OH. Instead, ether formation typically requires an oxidized, pre-functionalized carbon atom in R—X, which has a suitable leaving group X (X=halide, OC(O)R, $OSO_2R$, etc.) that is amenable to a displacement reaction with an alcohol R'OH to give the ether, R—OR'. Moreover, prior art methods typically require installation of the leaving group X on a pre-oxidized species (usually R—OH), and generate waste (base+HX). That said, in a rare example of stoichiometric C—H oxidation directly to form ethers, reaction of 2,4,6-trimethylphenol with stoichiometric $CuCl_2$ and $H_2O_2$ in isopropanol and in the presence of a base ($K_2CO_3$) gave an ether product. Sun, X. et al. (2008) *Catal. Today* 131:423-436.

SUMMARY OF THE INVENTION

One aspect of the invention is methods for the direct formation of ethers (R—OR') from alcohols, R'OH, and $sp^3$-hybridized C—H bonds in substrates, R—H. The methods of the invention directly convert C—H bonds in R—H to ethers, R—OR', by reaction with alcohols, R'OH. Advantageously, the methods of the invention minimize reaction steps, the handling of oxidized intermediates, and environmental impact.

Using alcohols (R'OH) as substrates, the methods of the invention are useful in the synthesis of ethers via C—H etherification of substrates R—H to give R—O—R'. The methods are general for the etherification of $sp^3$-hybridized C—H bonds. Etherification appears to proceed via a radical mechanism because benzylic, allylic and tertiary C—H bonds are often the most susceptible to oxidation. We have also demonstrated the use of aryl acetates for C—H to C-OAr bond formation. This strategy is useful when the RO—H bond itself is easily oxidized, such as in phenols. Moreover, the methods of the invention are useful in the preparation of C—S bonds from acetyl-protected thiols, MeC(O)SR, and disulfides, RSSR.

The methods of the invention may employ a copper-containing catalyst similar to β-diketiminato catalysts disclosed in WO 2008/073781, the entire contents of which are incorporated herein by reference. An example of a β-diketiminato catalyst, [$Cl_2NN$]Cu, is commercially available from Strem Chemicals. The use of a copper-containing catalyst as opposed to common catalysts based on noble metals is highly desirable from a cost and sustainability perspective.

An aspect of the invention is a method of forming an ether, comprising combining a substrate comprising a reactive C—H bond, an alcohol, an oxidizing agent, and a copper-containing catalyst, thereby forming an ether; wherein the copper-containing catalyst is represented by Formula I or an enantiomer, stereoisomer or diastereomer thereof:

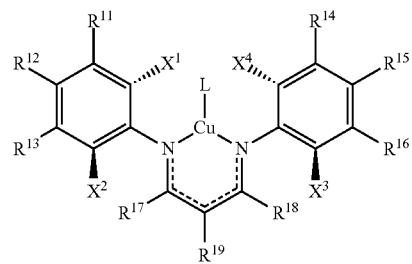

wherein:
$R^{11}$ to $R^{19}$ are independently selected from the group consisting of hydrogen, alkyl, aryl, aralkyl, halogen, cyano, nitro and trifluoromethyl;
$X^1$ to $X^4$ are independently selected from the group consisting of hydrogen, halogen, alkyl, perhaloalkyl and aryl; and
L is absent or a Lewis base.

An aspect of the invention is a method of generating an ether, comprising combining a substrate comprising a reactive C—H bond, an aryl acetate, an oxidizing agent, and a copper-containing catalyst, thereby forming an ether; wherein the copper-containing catalyst is represented by Formula I or an enantiomer, stereoisomer or diastereomer thereof:

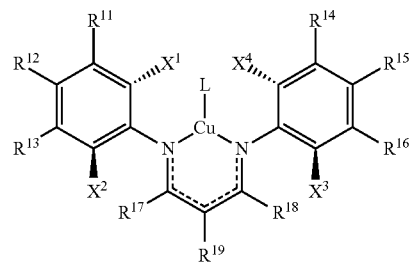

wherein:
$R^{11}$ to $R^{19}$ are independently selected from the group consisting of hydrogen, alkyl, aryl, aralkyl, halogen, cyano, nitro and trifluoromethyl;
$X^1$ to $X^4$ are independently selected from the group consisting of hydrogen, halogen, alkyl, perhaloalkyl and aryl; and
L is absent or a Lewis base.

An aspect of the invention is a method of forming a thioether, comprising combining a substrate comprising a reactive C—H bond, an acetyl-protected thiol, an oxidizing agent, and a copper-containing catalyst, thereby forming a thioether; wherein the copper-containing catalyst is represented by Formula I or an enantiomer, stereoisomer or diastereomer thereof:

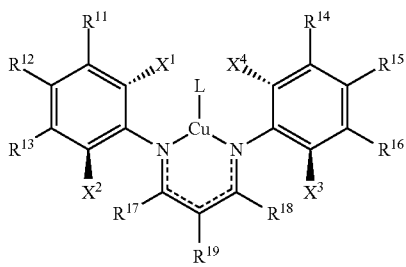

wherein:
R[11] to R[19] are independently selected from the group consisting of hydrogen, alkyl, aryl, aralkyl, halogen, cyano, nitro and trifluoromethyl;
X[1] to X[4] are independently selected from the group consisting of hydrogen, halogen, alkyl, perhaloalkyl and aryl; and
L is absent or a Lewis base.

An aspect of the invention is a method of forming a thioether, comprising combining a substrate comprising a reactive C—H bond, a disulfide, an oxidizing agent, and a copper-containing catalyst, thereby forming a thioether; wherein the copper-containing catalyst is represented by Formula I or an enantiomer, stereoisomer or diastereomer thereof:

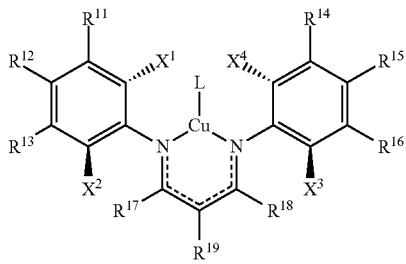

wherein:
R[11] to R[19] are independently selected from the group consisting of hydrogen, alkyl, aryl, aralkyl, halogen, cyano, nitro and trifluoromethyl;
X[1] to X[4] are independently selected from the group consisting of hydrogen, halogen, alkyl, perhaloalkyl and aryl; and
L is absent or a Lewis base.

In one embodiment, the copper-containing catalyst is

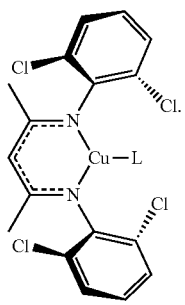

In one embodiment, the copper-containing catalyst is in the form $\{[Cl_2NN]Cu\}_2$(benzene):

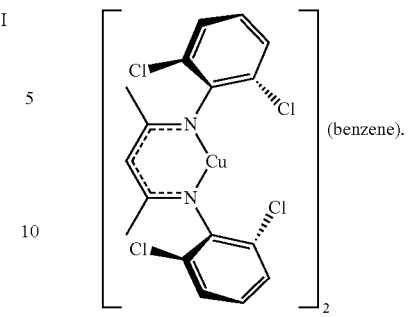

BRIEF DESCRIPTION OF THE DRAWINGS

FIG. 4 is a table showing representative results of reactions using various aliphatic alcohols and C—H substrates to form ethers in accordance with the invention. RT, room temperature.

DETAILED DESCRIPTION OF THE INVENTION

The invention generally concerns methods involving combining (a) a substrate comprising a reactive C—H bond, (b) an alcohol, thiol, acyl-protected phenol or thiophenol group, or a disulfide, (c) an oxidizing agent and (d) a copper-containing catalyst, thereby forming a product (e.g., an ether or thioether) with a covalent bond between the carbon of the reactive C—H bond and the O or the S of the reactive C—O or C—S bond.

An aspect of the invention concerns a method of copper-catalyzed formation of ethers (R—OR') from sp$^3$-hybridized C—H bonds in substrates (R—H), and alcohols (R'OH). Such reactions are referred to herein as C—H etherification reactions. The method can be represented, for example, by Scheme 1:

Scheme 1

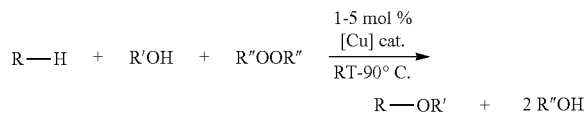

wherein R"OOR" represents a peroxide, RT denotes room temperature, and [Cu] cat. is a copper-containing catalyst, discussed below. This method of direct generation is in sharp contrast to the typical two-step method of ether synthesis known in the art:

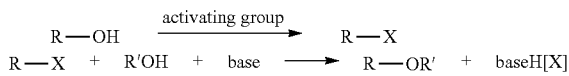

An aspect of the invention concerns a method of copper-catalyzed formation of ethers (R—OR') from $sp^3$-hybridized C—H bonds in suitable substrates (R—H) and acyl-protected phenols. The method can be represented, for example, by Scheme 2:

Scheme 2

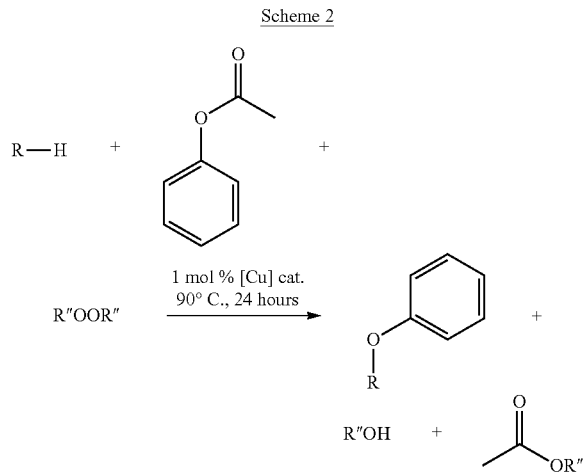

wherein R"OOR" represents a peroxide, and [Cu] cat. is a copper-containing catalyst, discussed below.

An aspect of the invention concerns a method of copper-catalyzed formation of thioethers (R—SR') from $sp^3$-hybridized C—H bonds in suitable substrates (R—H) and acyl-protected thiophenols. The method can be represented by, for example, Scheme 3:

Scheme 3

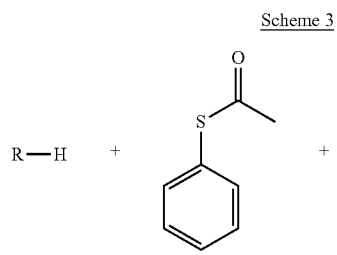

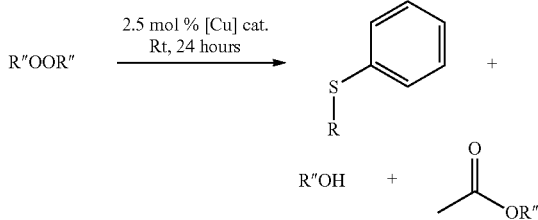

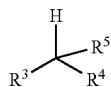

wherein R"OOR" represents a peroxide, RT denotes room temperature, and [Cu] cat. is a copper-containing catalyst, discussed below.

Figure 5:
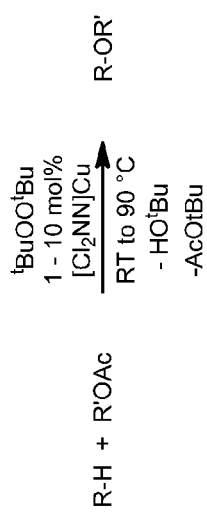
FIG. 5 is a table showing representative results of reactions using various acyl-protected phenols and thiophenols and C—H substrates to form ethers and thioethers, respectively, in accordance with the invention. RT, room temperature.
Figure 6:
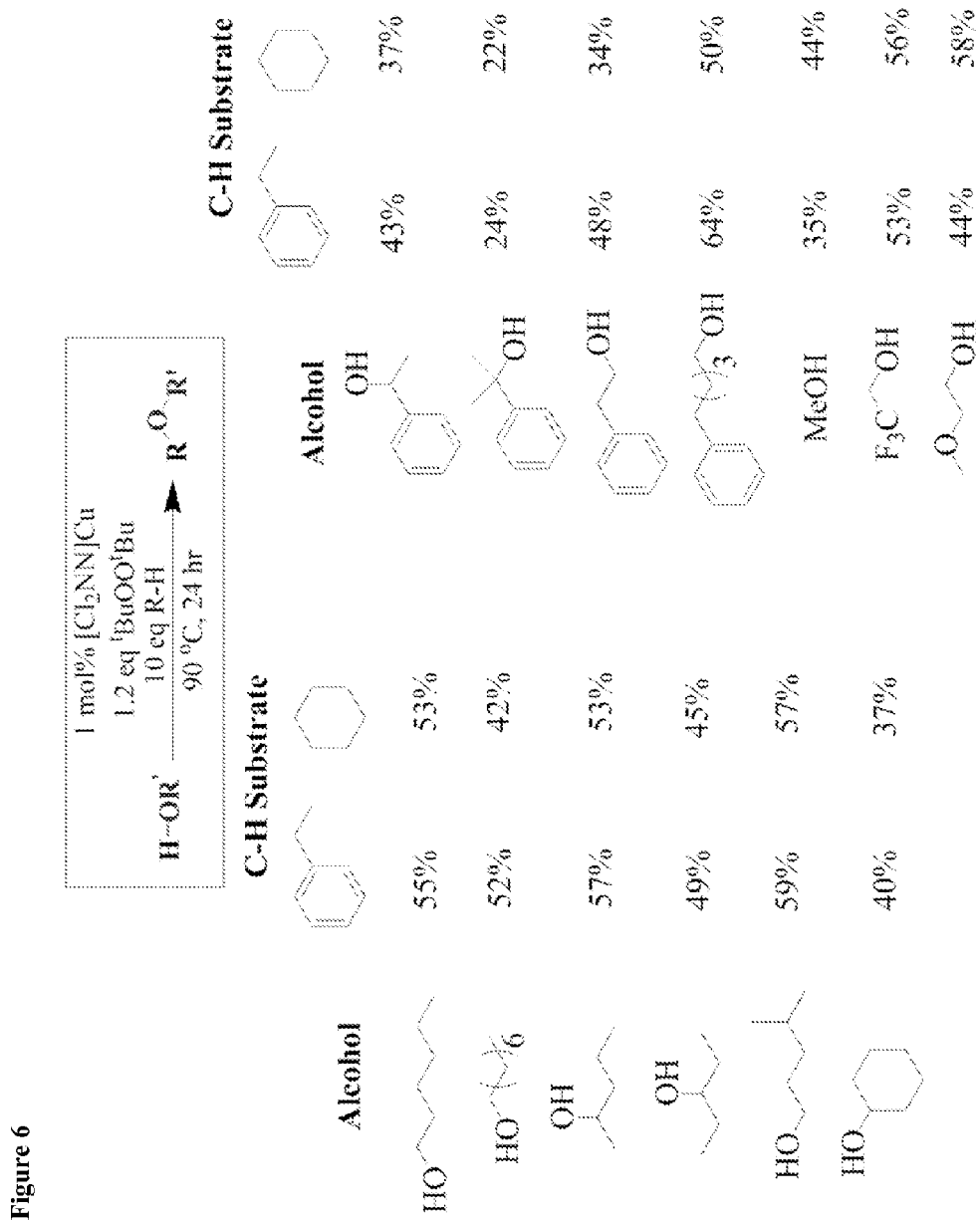
FIG. 6 is a table showing representative results of reactions using structurally diverse alcohols and C—H substrates to form ethers in accordance with the invention. Yields were obtained by $^1H$ NMR spectroscopy in a similar manner to those described more completely in the detailed experimental procedures found in the Examples.

A wide range of C—H bonds will be amenable to the C—H etherification reactions described herein, with selectivity likely to follow trends in C—H bond strength (weaker C—H bonds resulting in shorter reaction times). For instance, substrates which are amenable to the catalytic oxidation reactions described herein (and their resulting ether and thioether products) are shown in FIG. 4 and FIG. 5.

In certain embodiments, the substrate comprising a reactive C—H bond is represented by:

$$\underset{R^3}{\overset{H}{\diagdown}}\underset{R^4}{\overset{R^5}{\diagup}}$$

wherein, $R^3$ is alkyl, alkenyl, alkynyl, aryl, heteroaryl, aralkyl, heteroaralkyl, carbocyclyl, heterocyclyl, polycyclyl, carbonyl, ester or ether; $R^4$ is hydrogen, alkyl, alkenyl, alkynyl, aryl, heteroaryl, aralkyl, heteroaralkyl, carbocyclyl, heterocyclyl, polycyclyl, carbonyl, ester or ether; or $R^3$ and $R^4$ taken together are oxo (i.e., the substrate is an aldehdye: HC(=O)$R^5$); $R^5$ is hydrogen, alkyl, alkenyl, alkynyl, aryl, heteroaryl, aralkyl, heteroaralkyl, carbocyclyl, heterocyclyl, polycyclyl, carbonyl, ester or ether; and the substrate is optionally substituted with 1-3 substituents selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano.

In other embodiments, the substrate is a cyclopropane, cyclobutane, cyclopentane, cyclohexane, indane, 2-oxoindane, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactone, lactam, azetidinone, pyrrolidinone, sultam, or sultone; and the substrate is optionally substituted with 1-3 substituents selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano.

In certain embodiments, the substrate is selected from the group consisting of

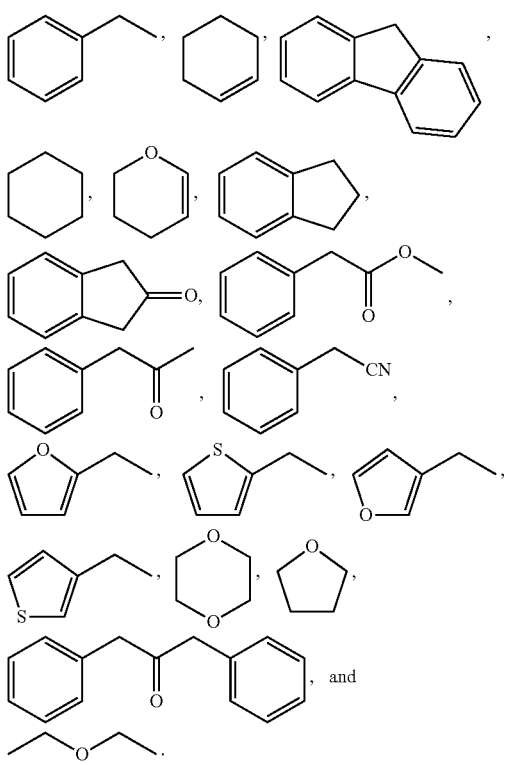

In certain embodiments, the alcohol is a primary alcohol, a secondary alcohol, or a tertiary alcohol. In certain other embodiments, the alcohol is a monohydric alcohol. In yet other embodiments, the alcohol is a polyhydric alcohol. In certain embodiments, the alcohol is a diol, triol, tetraol, pentol, or hexol. In certain embodiments, the alcohol is an aliphatic alcohol. In certain other embodiments, the alcohol is a saturated aliphatic or unsaturated aliphatic alcohol. In yet other embodiments, the alcohol is an allylic, homoallylic, doubly allylic, doubly homoallylic, propargylic, homopropargylic, doubly propargylic, doubly homopropargylic, benzylic, homobenzylic, doubly benzylic, or doubly homobenzylic alcohol. In certain embodiments, the alcohol is a glycol, a glycerol, an erythritol, a xylitol, a mannitol, an inositol, a menthol, or a naturally or non-naturally occurring sugar. In certain other embodiments, the alcohol is a cycloalkanol, a phenol or other aryl alcohol, or a heteroaryl alcohol. Any of the aforementioned alcohols may be optionally substituted with one or more halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano groups. Any of the aforementioned alcohols containing one or more prochiral $sp^3$ hybridized carbons may be chiral, meso, or achiral. Any of the aforementioned alcohols, if chiral, may be optically pure, racemic, or a mixture of diasteriomers or enantiomers.

In certain embodiments, the alcohol is selected from the group consisting of methanol, ethanol, isopropyl alcohol, butyl alcohol, isobutyl alcohol, t-butanol, pentanol, pentan-2-ol, pentan-3-ol, hexanol, heptanol, octanol, cyclopentanol, cyclohexanol, benzyl alcohol, 2-phenylethan-1-ol, 2-phenyl-propan-2-ol, 5-phenyl-pent-1-ol, 2,2,2-trifluoroethan-1-ol, and 2-methoxyethan-1-ol.

Ligands and Catalysts

Catalysts useful in accordance with the invention include copper present in the context of a bidentate or multidentate ligand. For example, ligands and catalysts useful in accordance with the invention comprise certain copper-based compounds previously described to be useful in C—H bond amination and olefin arizidination (see WO 2008/073781 and WO 2010/028159, the entire disclosures of which are incorporated herein by reference).

1. N-Aryl β-Diketiminate Catalysts. The entire family of N-aryl β-diketiminate catalysts, such as those represented by Formula I (below) may be used. With reference to the structure of Formula I, in certain embodiments the substituents $X^1$ to $X^4$ do not contain benzylic C—H bonds. In certain embodiments, aryl C—H bonds are present. $R^{17}$-$R^{19}$ may have H atoms; sample $R^{17}$-$R^{19}$ substituents include, but are not limited to, hydrogen, methyl, trifluoromethyl, phenyl and t-butyl. M is copper and L is a Lewis base, such as copper(benzene). As discussed below, the catalyst may be manipulated via electronic tuning to make it more or less electron-rich.

In addition, it has been observed that the N-aryl β-diketiminate catalysts aggregate upon isolation under certain preparation conditions. It is also proposed that certain aggregates are stable and may be used directly in amination reactions. A procedure for preparing and isolating one such aggregate, $\{[Cl_2NN]Cu\}_2(benzene)_{0.8}$, is provided herein. While the following catalysts of formula I are presented as monomers, the present invention also encompases the use of such catalysts as aggregates (such as dimers). The same is true for the other catalyst types (such as those of formula II or III) discussed below.

In certain embodiments, the copper-containing catalyst is represented by Formula I or an enantiomer, stereoisomer or diastereomer thereof:

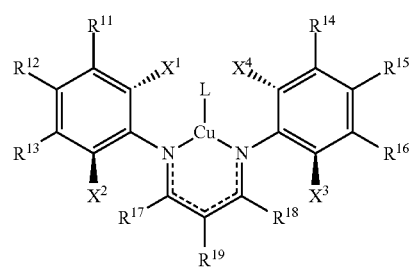

I wherein:
$R^{11}$ to $R^{19}$ are independently selected from the group consisting of hydrogen, alkyl, aryl, aralkyl, halogen, cyano, nitro and trifluoromethyl;
$X^1$ to $X^4$ are independently selected from the group consisting of hydrogen, halogen, alkyl, perhaloalkyl and aryl; and
L is absent or a Lewis base.

In certain embodiments, L, $X^1$ to $X^4$, and $R^{11}$ to $R^{19}$ each take any one of the aforementioned definitions, wherein $R^{17}$-$R^{19}$ represents independently for each occurrence hydrogen, methyl, trifluoromethyl, phenyl, or tert-butyl.

In certain embodiments, L, $X^1$ to $X^4$, and $R^{11}$ to $R^{19}$ each take any one of the aforementioned definitions, wherein $R^{17}$ and $R^{18}$ represent tert-butyl.

In certain embodiments, L, $X^1$ to $X^4$, and $R^{11}$ to $R^{19}$ each take any one of the aforementioned definitions, wherein $R^{17}$ and $R^{18}$ represent trifluoromethyl.

In certain embodiments, L, $X^1$ to $X^4$, and $R^{11}$ to $R^{19}$ each take any one of the aforementioned definitions, wherein $R^{19}$ is hydrogen.

In certain embodiments, L, $X^1$ to $X^4$, and $R^{11}$ to $R^{19}$ each take any one of the aforementioned definitions, wherein $X^1$ to $X^4$ are independently for each occurrence halogen or perfluoroalkyl.

In certain embodiments, L, $X^1$ to $X^4$, and $R^{11}$ to $R^{19}$ each take any one of the aforementioned definitions, wherein $X^1$ to $X^4$ are independently for each occurrence Cl, I, Br, or $CF_3$.

In certain embodiments, L, $X^1$ to $X^4$, and $R^{11}$ to $R^{19}$ each take any one of the aforementioned definitions, wherein $X^1$ to $X^4$ are Cl.

In certain embodiments, L, $X^1$ to $X^4$, and $R^{11}$ to $R^{19}$ each take any one of the aforementioned definitions, wherein $X^1$ to $X^4$ are $CF_3$.

In certain embodiments, L, $X^1$ to $X^4$, and $R^{11}$ to $R^{19}$ each take any one of the aforementioned definitions, wherein $X^1$ to $X^4$ are alkyl.

In certain embodiments, L, $X^1$ to $X^4$, and $R^{11}$ to $R^{19}$ each take any one of the aforementioned definitions, wherein $X^1$ to $X^4$ are methyl.

In certain embodiments, L, $X^1$ to $X^4$, and $R^{11}$ to $R^{19}$ each take any one of the aforementioned definitions, wherein $X^1$ to $X^4$ are isopropyl.

In certain embodiments, L, $X^1$ to $X^4$, and $R^{11}$ to $R^{19}$ each take any one of the aforementioned definitions, wherein $X^1$ to $X^4$ are aryl.

In certain embodiments, L, $X^1$ to $X^4$, and $R^{11}$ to $R^{19}$ each take any one of the aforementioned definitions, wherein $X^1$ to $X^4$ are phenyl.

In certain embodiments, L, $X^1$ to $X^4$, and $R^{11}$ to $R^{19}$ each take any one of the aforementioned definitions, wherein L is aromatic.

In certain embodiments, L, $X^1$ to $X^4$, and $R^{11}$ to $R^{19}$ each take any one of the aforementioned definitions, wherein L is toluene.

In certain embodiments, L, $X^1$ to $X^4$, and $R^{11}$ to $R^{19}$ each take any one of the aforementioned definitions, wherein L is benzene.

In certain embodiments, L, $X^1$ to $X^4$, and $R^{11}$ to $R^{19}$ each take any one of the aforementioned definitions, wherein L is O.

In certain embodiments, L, $X^1$ to $X^4$, and $R^{11}$ to $R^{19}$ each take any one of the aforementioned definitions, wherein $X_1$ to $X_4$ are independently for each occurrence Cl, and L is toluene.

In certain embodiments, L, $X^1$ to $X^4$, and $R^{11}$ to $R^{19}$ each take any one of the aforementioned definitions, wherein $X_1$ to $X_4$ are independently for each occurrence Cl, and L is benzene.

In certain embodiments, L, $X^1$ to $X^4$, and $R^{11}$ to $R^{19}$ each take any one of the aforementioned definitions, wherein $X_1$ to $X_4$ are independently for each occurrence $CF_3$, and L is toluene.

In certain embodiments, L, $X^1$ to $X^4$, and $R^{11}$ to $R^{19}$ each take any one of the aforementioned definitions, wherein $X_1$ to $X_4$ are independently for each occurrence $CF_3$, and L is benzene.

In one embodiment, L, $X^1$ to $X^4$, and $R^{11}$ to $R^{19}$ each take any one of the aforementioned definitions, wherein $R_1$-$R_6$ are independently for each occurrence H, $R_7$ and $R_8$ are independently for each occurrence Me, $R_9$ is H, $X_1$ to $X_4$ are independently for each occurrence Cl, and L is benzene. That is, in one embodiment, the catalyst is $\{[Cl_2NN]Cu\}_2$(benzene).

In certain embodiments, the copper-containing catalyst is selected from the group consisting of:

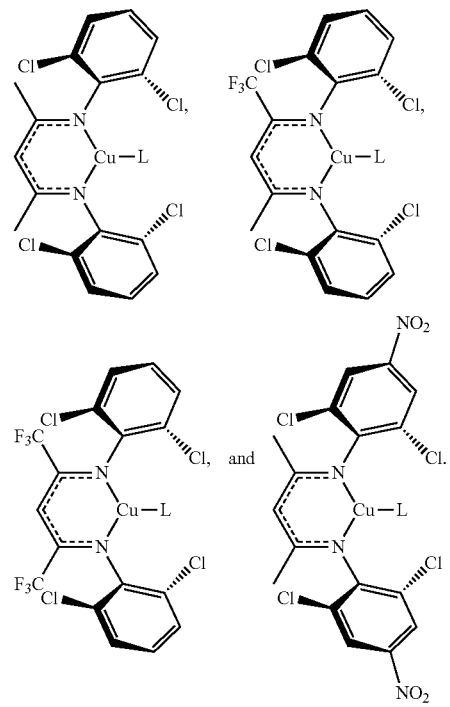

In certain embodiments, the copper-containing catalyst is selected from the group consisting of:

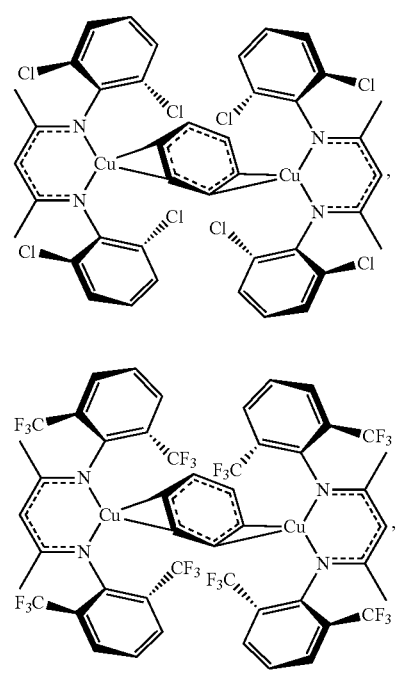

11
-continued
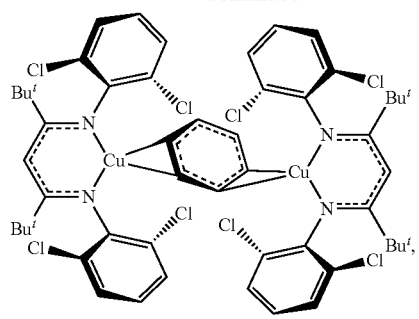
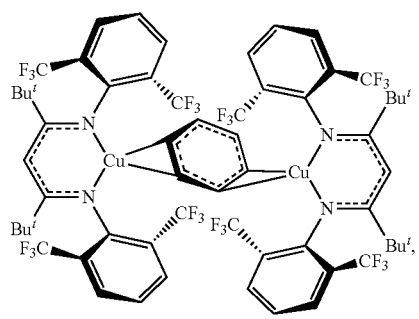
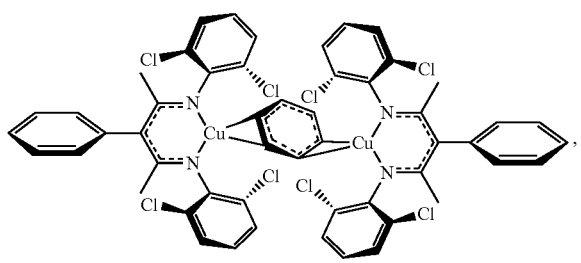
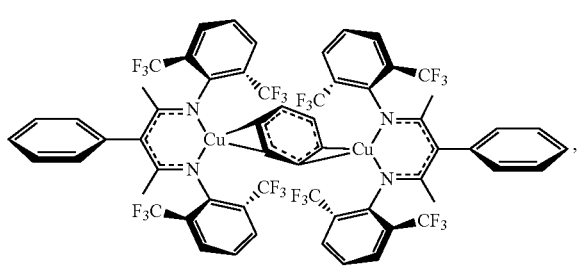
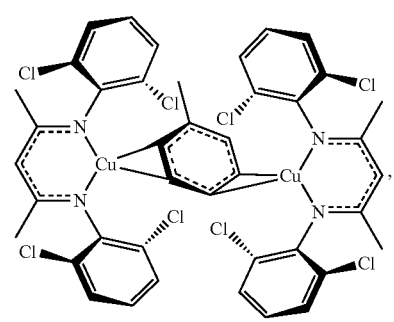
12
-continued
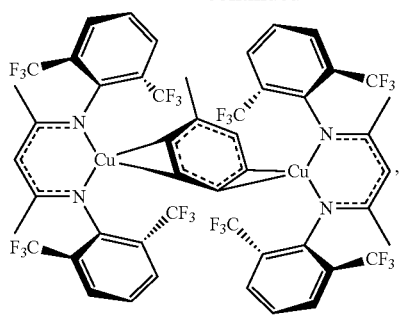
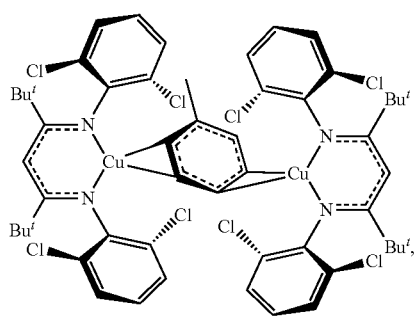
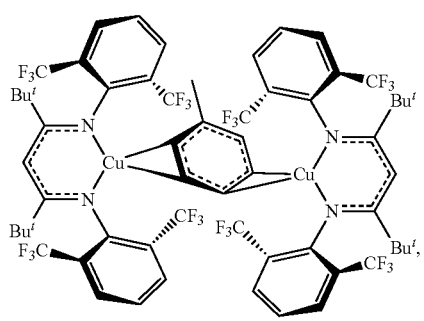
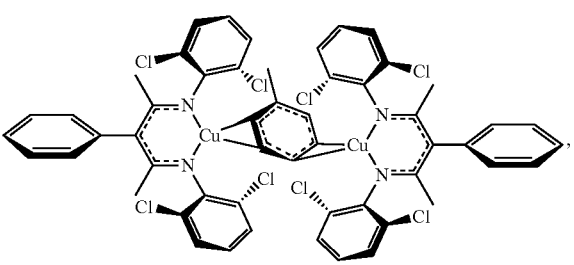
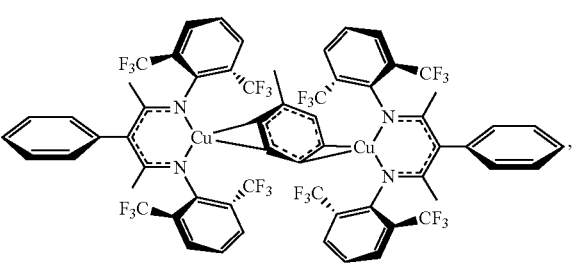

-continued
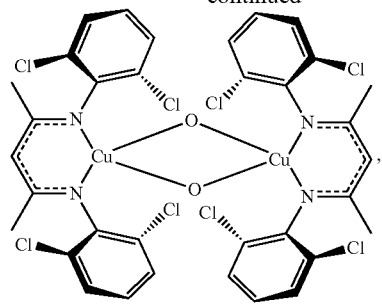
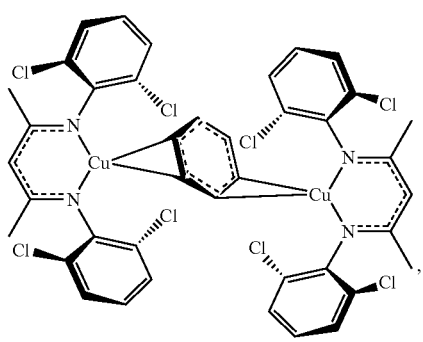
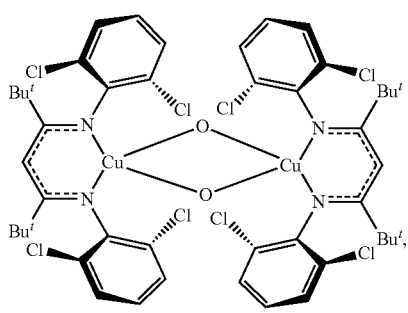
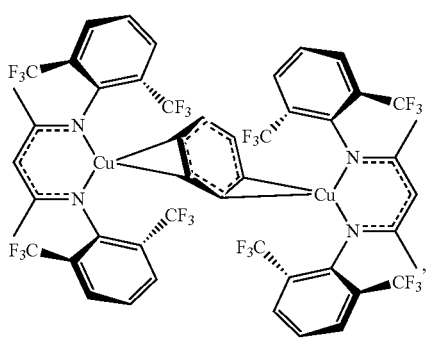
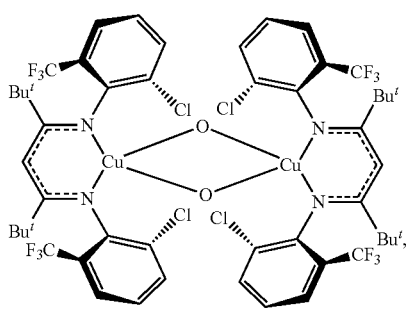
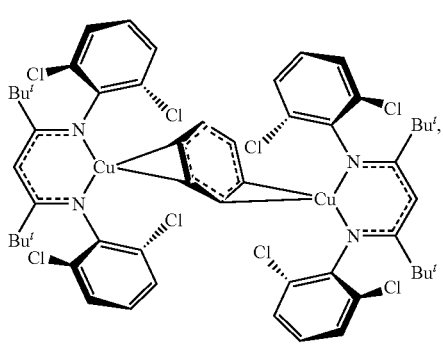
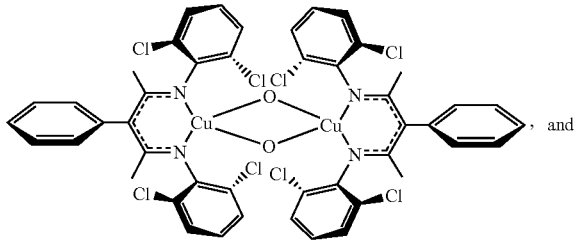, and
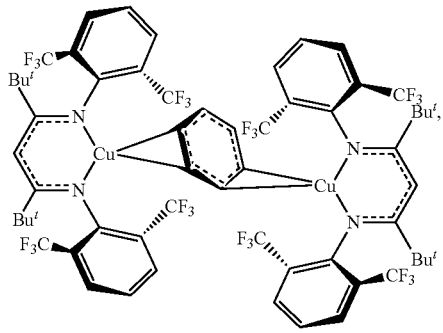
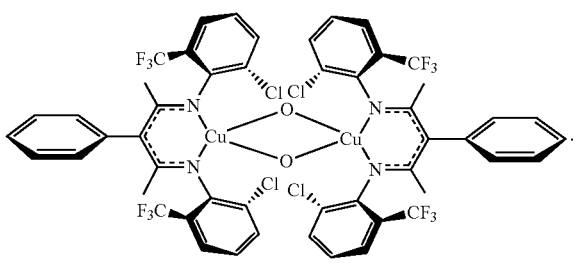.
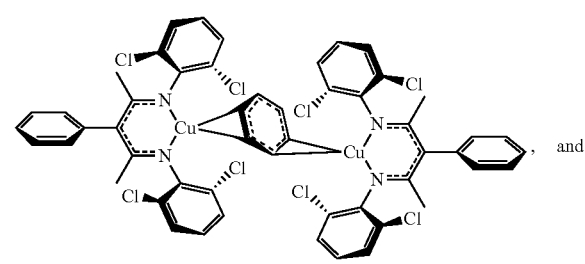, and
In certain embodiments, the copper-containing catalyst is selected from the group consisting of:

-continued

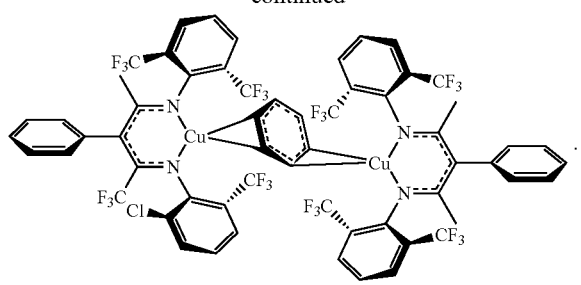

In one embodiment, the copper-containing catalyst is

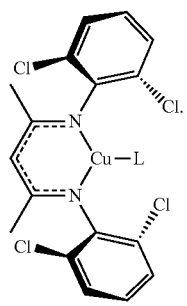

In one embodiment, the copper-containing catalyst is

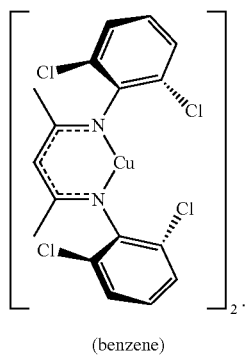

2. Anionic β-Diketiminate-Like Catalysts. In certain embodiments, the catalysts of the present invention may also be represented by Formula IIa or IIb (below).

In one embodiment, the copper-containing catalyst is represented by Formula IIa or an enantiomer, stereoisomer or diastereomer thereof:

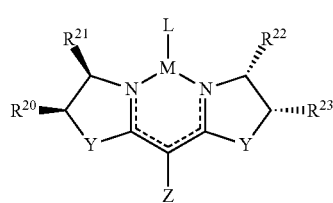

wherein $R^{20}$ is hydrogen, alkyl, aryl or heteroaryl; $R^{21}$ is alkyl, aryl or heteroaryl; $R^{22}$ is hydrogen, alkyl, aryl or heteroaryl; $R^{23}$ is alkyl, aryl or heteroaryl; Y is O, S, $CH_2$ or $CH_2CH_2$; Z is hydrogen or cyano; L is absent or a Lewis base; and M is copper.

In certain embodiments, L, Y, Z, M, and $R^{20}$ to $R^{23}$ each take any one of the aforementioned definitions, wherein $R^{20}$ is hydrogen.

In certain embodiments, L, Y, Z, M, and $R^{20}$ to $R^{23}$ each take any one of the aforementioned definitions, wherein $R^{20}$ is phenyl.

In certain embodiments, L, Y, Z, M, and $R^{20}$ to $R^{23}$ each take any one of the aforementioned definitions, wherein $R^{21}$ is phenyl.

In certain embodiments, L, Y, Z, M, and $R^{20}$ to $R^{23}$ each take any one of the aforementioned definitions, wherein $R^{22}$ is phenyl.

In certain embodiments, L, Y, Z, M, and $R^{20}$ to $R^{23}$ each take any one of the aforementioned definitions, wherein $R^{23}$ is hydrogen.

In certain embodiments, L, Y, Z, M, and $R^{20}$ to $R^{23}$ each take any one of the aforementioned definitions, wherein $R^{23}$ is phenyl.

In certain embodiments, L, Y, Z, M, and $R^{20}$ to $R^{23}$ each take any one of the aforementioned definitions, wherein Y is O.

In certain embodiments, L, Y, Z, M, and $R^{20}$ to $R^{23}$ each take any one of the aforementioned definitions, wherein Z is hydrogen.

In certain embodiments, L, Y, Z, M, and $R^{20}$ to $R^{23}$ each take any one of the aforementioned definitions, wherein Z is cyano.

In certain embodiments, L, Y, Z, M, and $R^{20}$ to $R^{23}$ each take any one of the aforementioned definitions, wherein M is copper(I).

In certain embodiments, L, Y, Z, M, and $R^{20}$ to $R^{23}$ each take any one of the aforementioned definitions, wherein M is copper(II).

In certain embodiments, L, Y, Z, M, and $R^{20}$ to $R^{23}$ each take any one of the aforementioned definitions, wherein L is absent.

In certain embodiments, L, Y, Z, M, and $R^{20}$ to $R^{23}$ each take any one of the aforementioned definitions, wherein L is solvent.

In certain embodiments, L, Y, Z, M, and $R^{20}$ to $R^{23}$ each take any one of the aforementioned definitions, wherein L is aromatic.

In certain embodiments, L, Y, Z, M, and $R^{20}$ to $R^{23}$ each take any one of the aforementioned definitions, wherein L is an olefin.

In certain embodiments, L, Y, Z, M, and $R^{20}$ to $R^{23}$ each take any one of the aforementioned definitions, wherein L is benzene.

In certain embodiments, the catalyst is selected from the group consisting of

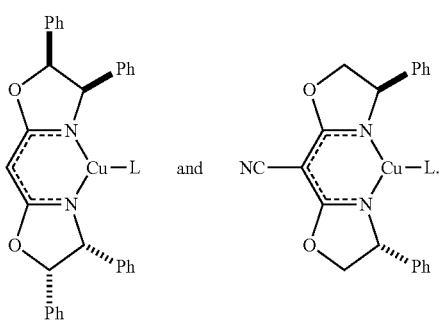

In one embodiment, the copper-containing catalyst is represented by Formula IIb or an enantiomer, stereoisomer or diastereomer thereof:

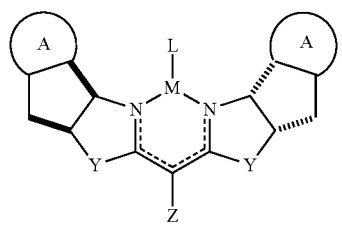

IIb wherein, A is aryl or heteroaryl; Y is O, S, $CH_2$ or $CH_2CH_2$; Z is hydrogen or cyano; L is absent or a Lewis base; and M is copper.

In certain embodiments, L, Y, Z, M, and A each take any one of the aforementioned definitions, wherein A is phenyl.

In certain embodiments, L, Y, Z, M, and A each take any one of the aforementioned definitions, wherein Y is O.

In certain embodiments, L, Y, Z, M, and A each take any one of the aforementioned definitions, wherein Z is hydrogen.

In certain embodiments, L, Y, Z, M, and A each take any one of the aforementioned definitions, wherein M is copper (I).

In certain embodiments, L, Y, Z, M, and A each take any one of the aforementioned definitions, wherein M is copper (II).

In certain embodiments, L, Y, Z, M, and A each take any one of the aforementioned definitions, wherein L is absent.

In certain embodiments, L, Y, Z, M, and A each take any one of the aforementioned definitions, wherein L is solvent.

In certain embodiments, L, Y, Z, M, and A each take any one of the aforementioned definitions, wherein L is aromatic.

In certain embodiments, L, Y, Z, M, and A each take any one of the aforementioned definitions, wherein L is an olefin.

In certain embodiments, L, Y, Z, M, and A each take any one of the aforementioned definitions, wherein L is alkyoxy.

In certain embodiments, L, Y, Z, M, and A each take any one of the aforementioned definitions, wherein L is t-butoxy.

In certain embodiments, the catalyst is

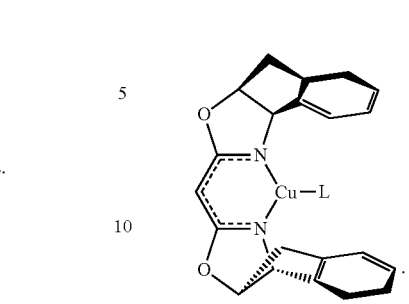

3. Catalysts Containing Neutral Ligands and Cationic Metal Sources. Neutral ligands when combined with cationic copper sources may also form active catalysts for C—H etherification. For instance, phenyl- and t-butyl-substituted bis(oxazoline) ligands (see III below) when combined in situ with $[Cu(NCMe)_4]BF_4$ result in active catalysts for C—H etherification. Since both bis(oxazolines) form active catalysts, it is anticipated that a broad class of poly(amines) and poly(imines) will work. Chiral bis(oxazolines) may also be used; the use of chiral ligands in general is discussed below.

In one embodiment, the copper-containing catalyst is represented by Formula III or an enantiomer, stereoisomer or diastereomer thereof:

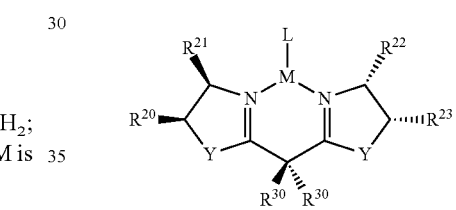

III wherein $R^{20}$ is hydrogen, alkyl, aryl or heteroaryl; $R^{21}$ is alkyl, aryl or heteroaryl; $R^{22}$ is hydrogen, alkyl, aryl or heteroaryl; $R^{23}$ is alkyl, aryl or heteroaryl; $R^{30}$ is alkyl or both $R^{30}$ taken together are a cycloakyl ring; Y is O, S, $CH_2$ or $CH_2CH_2$; L is a Lewis base; and M is copper.

In certain embodiments, L, Y, M, $R^{20}$ to $R^{23}$, and $R^{30}$ each take any one of the aforementioned definitions, wherein $R^{20}$ is hydrogen.

In certain embodiments, L, Y, M, $R^{20}$ to $R^{23}$, and $R^{30}$ each take any one of the aforementioned definitions, wherein $R^{21}$ is phenyl.

In certain embodiments, L, Y, M, $R^{20}$ to $R^{23}$, and $R^{30}$ each take any one of the aforementioned definitions, wherein $R^{21}$ is t-butyl.

In certain embodiments, L, Y, M, $R^{20}$ to $R^{23}$, and $R^{30}$ each take any one of the aforementioned definitions, wherein $R^{22}$ is phenyl.

In certain embodiments, L, Y, M, $R^{20}$ to $R^{23}$, and $R^{30}$ each take any one of the aforementioned definitions, wherein $R^{22}$ is t-butyl.

In certain embodiments, L, Y, M, $R^{20}$ to $R^{23}$, and $R^{30}$ each take any one of the aforementioned definitions, wherein $R^{23}$ is hydrogen.

In certain embodiments, L, Y, M, $R^{20}$ to $R^{23}$, and $R^{30}$ each take any one of the aforementioned definitions, wherein $R^{30}$ is alkyl.

In certain embodiments, L, Y, M, $R^{20}$ to $R^{23}$, and $R^{30}$ each take any one of the aforementioned definitions, wherein $R^{30}$ is methyl.

In certain embodiments, L, Y, M, $R^{20}$ to $R^{23}$, and $R^{30}$ each take any one of the aforementioned definitions, wherein Y is O.

In certain embodiments, L, Y, M, $R^{20}$ to $R^{23}$, and $R^{30}$ each take any one of the aforementioned definitions, wherein M is copper(I).

In certain embodiments, L, Y, M, $R^{20}$ to $R^{23}$, and $R^{30}$ each take any one of the aforementioned definitions, wherein M is copper(II).

In certain embodiments, L, Y, M, $R^{20}$ to $R^{23}$, and $R^{30}$ each take any one of the aforementioned definitions, wherein L is absent.

In certain embodiments, L, Y, M, $R^{20}$ to $R^{23}$, and $R^{30}$ each take any one of the aforementioned definitions, wherein L is solvent.

In certain embodiments, L, Y, M, $R^{20}$ to $R^{23}$, and $R^{30}$ each take any one of the aforementioned definitions, wherein L is aromatic.

In certain embodiments, L, Y, M, $R^{20}$ to $R^{23}$, and $R^{30}$ each take any one of the aforementioned definitions, wherein L is an olefin.

In certain embodiments, L, Y, M, $R^{20}$ to $R^{23}$, and $R^{30}$ each take any one of the aforementioned definitions, wherein L is NC(alkyl).

In certain embodiments, L, Y, M, $R^{20}$ to $R^{23}$, and $R^{30}$ each take any one of the aforementioned definitions, wherein L is NC(methyl).

In certain embodiments, the catalyst is selected from the group consisting of

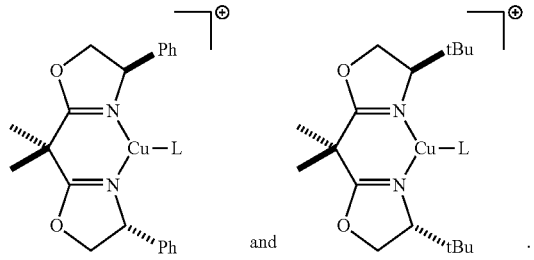

In one embodiment, the copper-containing catalyst is represented by Formula IV or an enantiomer, stereoisomer or diastereomer thereof:

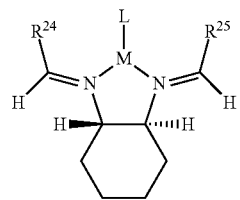

IV wherein $R^{24}$ is aryl or heteroaryl; $R^{25}$ is aryl or heteroaryl; L is a Lewis base; and M is copper.

In certain embodiments, L, M, $R^{24}$ and $R^{25}$ each take any one of the aforementioned definitions, wherein $R^{24}$ is phenyl optionally substituted with 1-3 substituents selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano.

In certain embodiments, L, M, $R^{24}$ and $R^{25}$ each take any one of the aforementioned definitions, wherein $R^{24}$ is a 2,6-disubstituted phenyl; and the substituents are selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano.

In certain embodiments, L, M, $R^{24}$ and $R^{25}$ each take any one of the aforementioned definitions, wherein $R^{24}$ is a 2,6-dihalo phenyl.

In certain embodiments, L, M, $R^{24}$ and $R^{25}$ each take any one of the aforementioned definitions, wherein $R^{25}$ is phenyl optionally substituted with 1-3 substituents selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano.

In certain embodiments, L, M, $R^{24}$ and $R^{25}$ each take any one of the aforementioned definitions, wherein $R^{25}$ is a 2,6-disubstituted phenyl; and the substituents are selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano.

In certain embodiments, L, M, $R^{24}$ and $R^{25}$ each take any one of the aforementioned definitions, wherein $R^{25}$ is a 2,6-dihalo phenyl.

In certain embodiments, L, M, $R^{24}$ and $R^{25}$ each take any one of the aforementioned definitions, wherein M is copper (I).

In certain embodiments, L, M, $R^{24}$ and $R^{25}$ each take any one of the aforementioned definitions, wherein M is copper (II).

In certain embodiments, L, M, $R^{24}$ and $R^{25}$ each take any one of the aforementioned definitions, wherein L is absent.

In certain embodiments, L, M, $R^{24}$ and $R^{25}$ each take any one of the aforementioned definitions, wherein L is solvent.

In certain embodiments, L, M, $R^{24}$ and $R^{25}$ each take any one of the aforementioned definitions, wherein L is aromatic.

In certain embodiments, L, M, $R^{24}$ and $R^{25}$ each take any one of the aforementioned definitions, wherein L is an olefin.

In certain embodiments, L, M, $R^{24}$ and $R^{25}$ each take any one of the aforementioned definitions, wherein L is NC(alkyl).

In certain embodiments, L, M, $R^{24}$ and $R^{25}$ each take any one of the aforementioned definitions, wherein L is NC(methyl).

In certain embodiments, the catalyst is

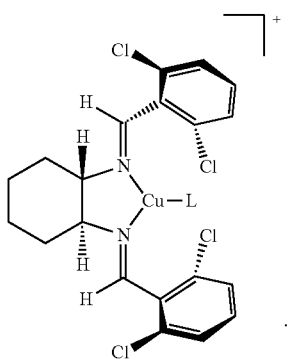

4. Catalysts Containing Non Anionic Neutral Ligands. A number of neutral ligands which may or may not be converted to anionic ligands may function as etherification catalysts. The catalysts must possess at least two arms that may simultaneously coordinate to a copper ion; they may possess more (e.g., tridendate ligands). Importantly, the catalysts should not possess $sp^3$-C—H bonds that may extend into the vicinity of the catalyst complex.

"Linked" Catalysts. Linked complexes may be especially useful in intramolecular cyclization reactions. Positioning the linker group distant from the metal binding site lessens the chemical demands as to the nature of the linking group.

5. Catalysts Prepared In Situ. Importantly, it is not necessary to use a pre-formed copper-containing catalyst consisting of one or more ligands and a copper ion. While some of the results provided herein relate to the direct use of the pre-synthesized β-diketiminato catalyst [Cl$_2$NN]Cu}$_2$(μ-benzene), active catalysts have also been prepared by mixing the β-diketimine ligand (H[Cl$_2$NN]) with CuO(t-Bu) or other suitable sources of copper.

Certain systems that employ more electron-withdrawing β-diketimine ligands, such as [Cl$_2$NN$_{F6}$] or [Cl$_2$NO$_2$NN] (see Figures), can likely be combined with Cu$_2$O (copper(I) oxide, which is inexpensive and not air-sensitive) to generate the active catalyst [Cl$_2$NN$_{F6}$]Cu or [Cl$_2$NO$_2$NN]Cu.

In certain embodiments, an active catalyst may be formed from an air-stable copper(II) complex bearing the desired ligand, such as {[Cl$_2$NN]Cu}$_2$(μ-OH)$_2$. Many copper(II) complexes exhibit greater air-stability than their copper(I) counterparts, making copper(II) an attractive metal for the storage and use of the catalysts.

6. Catalyst Optimization. Ligand substituents may be chosen to optimize the reactivity of the catalyst and the catalyst's stability; the catalyst may be tuned. In general, "tuning" refers to both altering the steric bulk of the ligand to limit the approach of the substrate, utilizing steric repulsions between the substrate and ligand substituents, and altering the electronic characteristics of the ligand to influence electronic interactions between the substrate and the ligand, as well as the rate and mechanism of the catalyzed reaction.

In addition, the choice of substituent may also affect catalyst stability; in general, bulkier substituents are found to provide higher catalyst turnover numbers. Furthermore, the choice of substituent on the ligand can also be used to influence the solubility of the catalyst in a particular solvent system.

As mentioned briefly above, the choice of ligand substituents can also affect the electronic properties of the catalyst. Substitution of the ligand with electron-rich (electron-donating) moieties (including, for example, alkoxy or amino groups) increases the electron density of the ligand and at the metal center. Conversely, electron-withdrawing moieties (for example, chloro or trifluoromethyl groups) on the ligand result in lower electron density of the ligand and metal center. Choice of substituents thus makes possible the "tuning" of the reaction rate.

For example, since the presence of electron-withdrawing substituents has been shown to increase the reactivity of many C—H etherification catalysts, adding CF$_3$ groups to the backbone of the catalyst may yield improved catalysts. Literature procedures have been used to prepare the corresponding o-Me$_2$Ph derivatives with these fluorinated backbones.

7. Chiral Ligands. Numerous chiral ligands exist for a host of established asymmetric transformations catalyzed by copper salts. In particular, many of these ligands are C$_2$-symmetric diamines or diiminates bearing strong similarity to the successful β-diketiminates described herein.

Methods of the Invention

An aspect of the invention concerns a method of copper-catalyzed formation of ethers (R—OR') from $sp^3$-hybridized C—H bonds in substrates (R—H) and alcohols (R'OH). Such reactions are referred to herein as C—H etherification reactions. The method can be represented, for example, by Scheme 1:

Scheme 1

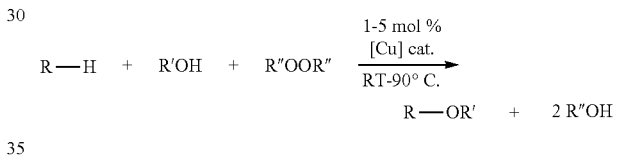

wherein R—H represents a substrate comprising a reactive C—H bond, discussed above; R'OH represents a first (i.e., reactant) alcohol; R"OOR" represents a peroxide (an oxidizing agent), R—OR' represents an ether; R"OH represents a second (i.e., product) alcohol; RT –90° C. denotes a range of temperature from room temperature to 90° C.; and [Cu] cat. is a copper-containing catalyst, i.e., any of the copper-containing catalysts discussed above.

An aspect of the invention concerns a method of copper-catalyzed formation of ethers (R—OR') from $sp^3$-hybridized C—H bonds in suitable substrates (R—H) and acyl-protected phenols. The method can be represented by, for example, Scheme 2:

Scheme 2

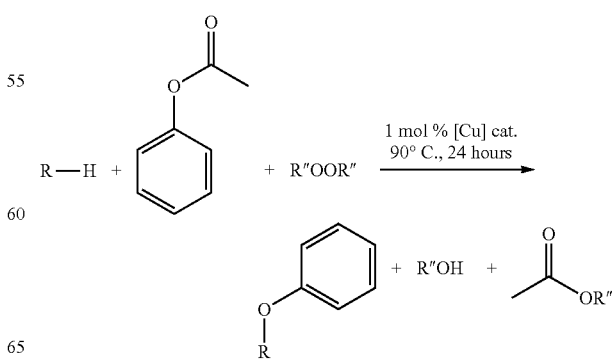

wherein R—H represents a substrate comprising a reactive C—H bond, discussed above; R"OOR" represents a peroxide (an oxidizing agent); R"OH represents a (product) alcohol; and [Cu] cat. is a copper-containing catalyst, i.e., any of the copper-containing catalysts discussed above.

An aspect of the invention concerns a method of copper-catalyzed formation of thioethers (R—SR') from $sp^3$-hybridized C—H bonds in suitable substrates (R—H) and acyl-protected thiophenols. The method can be represented by, for example, Scheme 3:

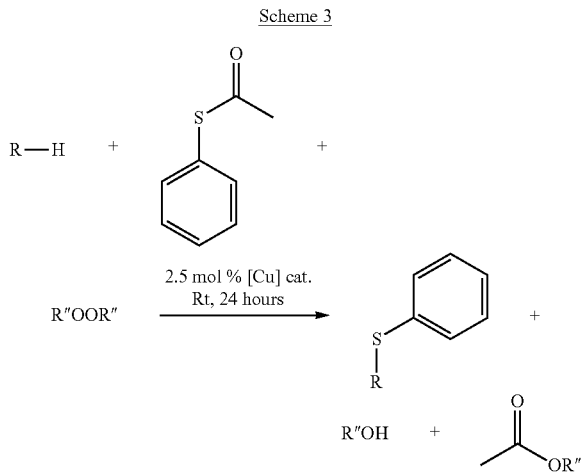

wherein R—H represents a substrate comprising a reactive C—H bond, discussed above; R"OOR" represents a peroxide (an oxidizing agent); RT denotes room temperature; R"OH represents a (product) alcohol; and [Cu] cat. is a copper-containing catalyst, i.e., any of the copper-containing catalysts discussed above.

In certain embodiments, the present invention relates to any one of the aforementioned methods and attendant definitions, wherein the oxidizing agent is selected from the group consisting of peroxides, oxygen, halogens, pseudo-halogen compounds, hypervalent iodide compounds, benzoquinones, and inorganic oxidation couples.

In certain embodiments, the present invention relates to any one of the aforementioned methods and attendant definitions, wherein the oxidizing agent is a peroxide represented by:

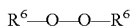

(or, equivalently, $R^6OOR^6$) wherein $R^6$ is independently for each occurrence hydrogen, alkyl, alkenyl, alkynyl, aryl, heteroaryl, aralkyl or heteroaralkyl. In certain embodiments, the two instances of $R^6$ are identical.

In certain embodiments, the present invention relates to any one of the aforementioned methods and attendant definitions, wherein at least one $R^6$ is alkyl. In certain embodiments, the present invention relates to any one of the aforementioned methods and attendant definitions, wherein each $R^6$ is alkyl. In certain embodiments, the present invention relates to any one of the aforementioned methods and attendant definitions, wherein each $R^6$ is an identical alkyl.

In certain embodiments, the present invention relates to any one of the aforementioned methods and attendant definitions, wherein at least one $R^6$ is tert-butyl. In certain embodiments, the present invention relates to any one of the aforementioned methods and attendant definitions, wherein each $R^6$ is tert-butyl.

In certain embodiments, the present invention relates to any one of the aforementioned methods and attendant definitions, wherein the reaction is run in neat substrate.

In certain embodiments, the present invention relates to any one of the aforementioned methods and attendant definitions, wherein the reaction takes place in a solvent.

In certain embodiments, the present invention relates to any one of the aforementioned methods and attendant definitions, wherein the solvent is selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol and propyl acetate In certain embodiments, the present invention relates to any one of the aforementioned methods and attendant definitions, wherein the solvent is anisole.

In certain embodiments, the present invention relates to any one of the aforementioned methods and attendant definitions, wherein the reaction is run at a temperature between about 20° C. and about 100° C.

In certain embodiments, the present invention relates to any one of the aforementioned methods and attendant definitions, wherein the reaction is run at a temperature between about 20° C. and about 30° C. In certain embodiments, the present invention relates to any one of the aforementioned methods and attendant definitions, wherein the reaction is run at room temperature In certain embodiments, the present invention relates to any one of the aforementioned methods and attendant definitions, wherein the reaction is run at a temperature between about 50° C. and about 100° C.

In certain embodiments, the present invention relates to any one of the aforementioned methods and attendant definitions, wherein the reaction is run at a temperature of about 80° C.

Catalyst Loading. A wide range of catalyst loadings can be used for the etherification reactions described herein. In certain embodiments, the catalyst is present in less than about 70 mol % relative to the substrate. In certain embodiments, the catalyst is present in less than about 60 mol % relative to the substrate. In certain embodiments, the catalyst is present in less than about 50 mol % relative to the substrate. In certain embodiments, the catalyst is present in less than about 40 mol % relative to the substrate. In certain embodiments, the catalyst is present in less than about 30 mol % relative to the substrate. In certain embodiments, the catalyst is present in less than about 20 mol % relative to the substrate. In certain embodiments, the catalyst is present in less than about 10 mol % relative to the substrate. In certain embodiments, the catalyst is present in less than about 5 mol % relative to the substrate. In certain embodiments, the catalyst is present in less than about 2.5 mol % relative to the substrate. In certain embodiments, the catalyst is present in less than about 1 mol % relative to the substrate.

Yields. In certain embodiments, the present invention relates to any one of the aforementioned methods and attendant definitions, wherein the product is formed in a yield of at least about 10%. In certain embodiments, the present invention relates to any one of the aforementioned methods and attendant definitions, wherein the product is formed in a yield of at least about 20%. In certain embodiments, the present invention relates to any one of the aforementioned methods and attendant definitions, wherein the product is formed in a yield of at least about 30%. In certain embodiments, the present invention relates to any one of the aforementioned methods and attendant definitions, wherein the product is formed in a yield of at least about 40%. In certain embodiments, the present invention relates to any one of the aforementioned methods and attendant definitions, wherein the product is formed in a yield of at least about 50%. In certain embodiments, the present invention relates to any one of the aforementioned methods and attendant definitions, wherein the product is formed in a yield of at least about 60%. In certain embodiments, the present invention relates to any one of the aforementioned methods and attendant definitions, wherein the product is formed in a yield of at least about 70%. In certain embodiments, the present invention relates to any one of the aforementioned methods and attendant definitions, wherein the product is formed in a yield of at least about 80%. In certain embodiments, the present invention relates to any one of the aforementioned methods and attendant definitions, wherein the product is formed in a yield of at least about 90%. In certain embodiments, the present invention relates to any one of the aforementioned methods and attendant definitions, wherein the product is formed in a yield of at least about 95%.

The etherification reactions of the present invention may be performed under a wide range of conditions, though it will be understood that the solvents and temperature ranges recited herein are not limitative and only correspond to one mode of the process of the invention.

In general, it will be desirable that reactions are run using mild conditions which will not adversely affect the substrate, the alcohol, the catalyst, or the product. For example, the reaction temperature influences the speed of the reaction, as well as the stability of the reactants, products, and catalyst. The reactions will usually be run at temperatures in the range of about −78° C. to about 200° C., in the range about 0° C. to about 100° C., in the range about 20° C. to about 30° C., or in the range about 50° C. to about 100° C.

In general, the etherification reactions of the present invention are carried out in a liquid reaction medium. The reactions may be run without addition of solvent. Alternatively, the reactions may be run in an inert solvent, e.g., one in which the reaction ingredients, including the catalyst, are substantially soluble. In some embodiments, the reactions can be run in a combination of two or more solvents.

The most environmentally friendly process will use little or no solvent as process conditions allow. It is possible to run the reaction in some cases without any solvent (e.g., morpholine, t-butylperoxide, ethylbenzene). In these cases, the reaction components form a liquid mixture at or above room temperature. (Caution—lack of reaction solvent may cause an exotherm when catalyst is added to mixture.)

In certain embodiments, the substrate itself may be used as a solvent. For instance, high yields of ethylbenzene etherification have been demonstrated using ethylbenzene as a solvent. Separation of the product from solvent is facilitated by the significant difference in chemical properties of the substrate/solvent as compared to the ether product.

An ideal solvent for the process does not undergo any reaction during the catalytic process except possibly weak, reversible binding to copper-containing catalyst. Solvents that do not have C—H bonds on the strength of benzyl and allylic C—H bonds (e.g., 88 kcal/mol and lower) may be appropriate for the etherification reaction. For instance, benzene (C—H bond strength=112.9 kcal/mol) is an appropriate solvent.

Provided that there is a suitable difference in the strength and kinetic availability of the substrate C—H bond for etherification, linear hydrocarbons such as hexane and heptane may prove useful solvents. More polar solvents such as ethers may be employed.

Ideally, the process employs one of the Class 3 solvents representing the least toxicity and environmental impact. Class 3 solvents include acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol and propyl acetate. Of these, anisole is particularly promising. It has a C—H bond strength ($OCH_3$) of 11 kcal/mol greater than ethylbenzene. With a boiling point of 154° C., it is not particularly volatile. Separations of ether products are straightforward from the solvent. Other promising solvents include tert-butylmethyl ether (MTBE), ethyl acetate, ethyl ether, heptane, methyl acetate, methyl ethyl ketone, pentane, and propyl acetate. All of these solvents possess C—H bonds whose weakest C—H bond strengths are about 8-10 kcal/mol higher than a benzylic or allylic C—H bond targeted in this C—H etherification reaction.

The invention also contemplates reaction in a biphasic mixture of solvents, in an emulsion or suspension, or reaction in a lipid vesicle or bilayer. In certain embodiments, one may perform the etherification reactions in the solid phase.

In certain embodiments, one may perform the reactions under an inert atmosphere of a gas such as nitrogen or argon.

The methods of the present invention can be conducted in continuous, semi-continuous, or batch fashion and may involve a liquid recycle and/or gas recycle operation as desired. The processes of this invention may be conducted in batch fashion. Likewise, the manner or order of addition of the reaction ingredients, catalyst, and solvent are also not critical and may be accomplished in any conventional fashion.

The reaction can be conducted in a single reaction zone or in a plurality of reaction zones, in series, or in parallel, or it may be conducted batchwise or continuously in an elongated tubular zone or series of such zones. The materials of construction employed should be inert to the starting materials during the reaction, and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the copper-ligand complex catalyst. When complete conversion is not desired or not obtainable, the starting materials can be separated from the product and then recycled back into the reaction zone.

The processes may be conducted in glass-lined, stainless steel, or similar type reaction equipment. The reaction zone may be fitted with one or more internal and/or external heat exchanger(s) in order to control undue temperature fluctuations, or to prevent any possible "runaway" reaction temperatures.

Furthermore, the catalyst can be immobilized or incorporated into a polymer or other insoluble matrix by, for example, derivatization with one or more of substituents of the ligand. The immobilized ligands can be complexed with copper to form the catalyst. The catalyst, particularly an "aged" catalyst, is easily recovered after the reaction as, for instance, by filtration or centrifugation.

In addition, since formal reductive elimination of the oxidized takes place within the coordination sphere of a single metal center, control over enantioselectivity may be levied with the selection of appropriate chiral ligands.

DEFINITIONS

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

For purposes of this invention, the chemical elements are identified in accordance with the Periodic Table of the Elements, CAS version, Handbook of Chemistry and Physics, 67th Ed., 1986-87, inside cover.

A "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an enantiomeric excess (ee) for a particular enantiomer that is larger than the ee of the reaction lacking the chiral catalyst.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The term "reaction product" or "product" means a compound which results from the reaction of the catalyst and substrate. In general, the term "reaction product" will be used herein to refer to a stable, isolable compound, and not to unstable intermediates or transition states.

The term "catalytic amount" is recognized in the art and means a substoichiometric amount relative to a reactant. As used herein, a catalytic amount means from 0.0001 to 90 mole percent relative to a reactant, more preferably from 0.001 to 50 mole percent, still more preferably from 0.01 to 10 mole percent, and even more preferably from 0.1 to 5 mole percent relative to a reactant.

As discussed more fully herein, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

% Enantiomeric Excess $A$ (ee)=(% Enantiomer $A$)−(% Enantiomer $B$)

where A and B are the enantiomers formed. Additional terms that are used in conjunction with enatioselectivity include "optical purity" or "optical activity". An enantioselective reaction yields a product with an ee greater than zero. Preferred enantioselective reactions yield a product with an ee greater than 20%, more preferably greater than 50%, even more preferably greater than 70%, and most preferably greater than 80%.

A diastereoselective reaction converts a chiral reactant (which may be racemic or enantiomerically pure) to a product enriched in one diastereomer. If the chiral reactant is racemic, in the presence of a chiral non-racemic reagent or catalyst, one reactant enantiomer may react more slowly than the other. This class of reaction is termed a kinetic resolution, wherein the reactant enantiomers are resolved by differential reaction rate to yield both enantiomerically-enriched product and enantiomerically-enriched unreacted substrate. Kinetic resolution is usually achieved by the use of sufficient reagent to react with only one reactant enantiomer (i.e., one-half mole of reagent per mole of racemic substrate). Examples of catalytic reactions which have been used for kinetic resolution of racemic reactants include the Sharpless epoxidation and the Noyori hydrogenation.

The term "non-racemic" with respect to the chiral catalyst, means a preparation of catalyst having greater than 50% of a given enantiomer, more preferably at least 75%. "Substantially non-racemic" refers to preparations of the catalyst which have greater than 90% ee for a given enantiomer of the catalyst, more preferably greater than 95% ee.

The term "$Cl_2NN$" refers to a moiety represented by the general formula:

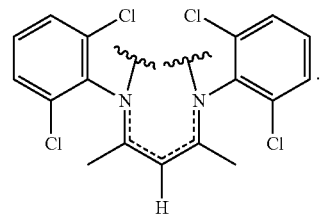

The term "$Cl_2NN_{F6}$" refers to a moiety represented by the general formula:

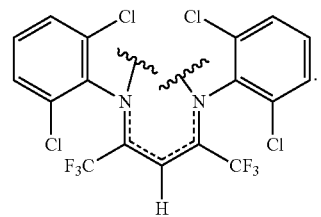

The term "Cl$_2$NO$_2$NN" refers to a moiety represented by the general formula:

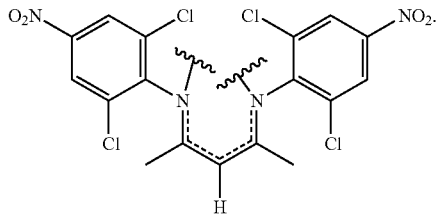

An "aliphatic" compound as used herein refers to an acyclic (e.g., straight- or branched-chain) or cyclic non-aromatic carbon-containing compound. Aliphatic compounds in general include alkanes (e.g., methane, ethane), alkenes (e.g., ethylene), and alkynes (e.g., acetylene).

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 of fewer. Likewise, preferred cycloalkyls have from 4-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

The term "alcohol" is art-recognized and refers to any substance having an OH group attached to a carbon.

The terms "alkenyl" and "alkynyl" refer to unsaturated aliphatic groups analogous in length and possible substitution to the alkyls described above, but which contain at least one double or triple carbon-carbon bond, respectively.

As used herein, the term "halogen" designates —F, —Cl, —Br or —I.

As used herein, the term "hydroxyl" means —OH.
As used herein, the term "nitro" means —NO$_2$.
As used herein, the term "thiol" means —SH.
As used herein, the term "sulfonyl" means —SO$_2$—.
As used herein, the term "disulfide" refers to any chemical compound that comprises a covalently linked pair of sulfur atoms (disulfide bond), e.g., diphenyl disulfide (C$_6$H$_5$—S—S—C$_6$H$_5$).

The terms "amine" and "amino" are art-recognized and refer to both unsubstituted and substituted amines, e.g., a moiety that can be represented by the general formula:

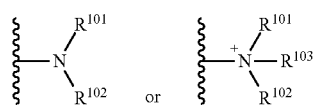

wherein $R^{101}$, $R^{102}$ and $R^{103}$ each independently represent hydrogen, alkyl, alkenyl, alkynyl, aryl, heteroaryl, —(CH$_2$)$_m$R$^{200}$, wherein m is an integer 1-10 and $R^{200}$ represents a group permitted by the rules of valence, such as hydrogen, alkyl, alkenyl, alkynyl, aryl, and heteroaryl.

The term "amino" also includes "acylamino," which is art-recognized and refers to a moiety that can be represented by the general formula:

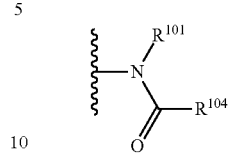

wherein $R^{1011}$ is as defined above, and $R^{104}$ represents hydrogen, alkyl, alkenyl, alkynyl, aryl, heteroaryl or —(CH$_2$)$_m$R$^{200}$, wherein m and $R^{200}$ are defined above.

The term "amido" is art-recognized as an amino-substituted carbonyl and includes a moiety that can be represented by the general formula:

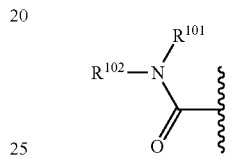

wherein $R^{101}$ and $R^{102}$ are as defined above.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$^{200}$, wherein m and $R^{200}$ are defined above. Representative alkylthio groups include methylthio and ethylthio.

The term "carbonyl" is art-recognized and includes such moieties as can be represented by the general formula:

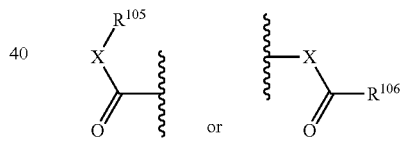

wherein X is a bond or represents an oxygen or a sulfur, and $R^{105}$ represents a hydrogen, alkyl, alkenyl, alkynyl, aryl, heteroaryl or —(CH$_2$)$_m$R$^{200}$, wherein m and $R^{200}$ are defined above, or a pharmaceutically acceptable salt, and $R^{106}$ represents hydrogen, alkyl, alkenyl, alkynyl, aryl, heteroaryl or —(CH$_2$)$_m$R$^{200}$, wherein m and $R^{200}$ are defined above. Where X is an oxygen and $R^{105}$ or $R^{106}$ is not hydrogen, the formula represents an "ester". Where X is an oxygen and $R^{105}$ is as defined above, the moiety is referred to herein as a carboxyl group, and particularly when $R^{105}$ is a hydrogen, the formula represents a "carboxylic acid". Where X is an oxygen and $R^{106}$ is hydrogen, the formula represents a "formate". In general, where the oxygen atom of the above formula is replaced by sulfur, the formula represents a "thiolcarbonyl" group. Where X is a sulfur and $R^{105}$ or $R^{106}$ is not hydrogen, the formula represents a "thiolester." Where X is a sulfur and $R^{105}$ is hydrogen, the formula represents a "thiolcarboxylic acid." Where X is a sulfur and $R^{106}$ is hydrogen, the formula represents a "thiolformate." On the other hand, where X is a bond and $R^{105}$ is not hydrogen, the above formula represents a "ketone" group. Where X is a bond, and $R^{106}$ is hydrogen, the above formula represents an "aldehyde" group.

The terms "alkoxyl" or "alkoxy" as used herein refer to an alkyl group, as defined above, having an oxygen radical attached thereto. Representative alkoxyl groups include methoxy, ethoxy, propyloxy, t-butoxy and the like.

An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, and —$(CH_2)_m$—$R^{200}$, where m and $R^{200}$ are as defined above.

The term "aryl" as used herein includes 4-, 5-, 6- and 7-membered single-ring aromatic groups which may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl". The aromatic ring can be substituted at one or more ring positions with such substituents as described above, as for example, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, —$(CH_2)_m$—$R^{200}$, where m and $R^{200}$ are as defined above, fluoroalkyl, trifluoromethyl, cyano, or the like.

The term "heteroatom" as used herein means an atom of any element other than carbon or hydrogen. Preferred heteroatoms are nitrogen, oxygen, sulfur, phosphorus and selenium. In one embodiment, a heteroatom is selected from nitrogen, oxygen, and sulfur. In one embodiment, a heteroatom is selected from nitrogen and oxygen. In one embodiment, a heteroatom is nitrogen. In one embodiment, a heteroatom is oxygen.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

The invention now being generally described, it will be more readily understood by reference to the following, which is included merely for purposes of illustration of certain aspects and embodiments of the present invention, and is not intended to limit the invention.

EXAMPLES

Example 1

Synthesis of $\{[Cl_2NN]Cu\}_2$(benzene)

A solution of KO$^t$Bu (3.53 g, 31.6 mmol, ca. 20 mL THF) was added to a slurry of CuI (5.99 g, 31.6 mmol, in ca. 80 mL THF) and stirred overnight. The solution started milky white and developed a slight gray tint over time. The reaction was filtered over Celite®. To the filtrate was added benzene (28 mL, 316 mmol) and a solution of H[$Cl_2NN$] (12.25 g, 31.57 mmol, in ca. 25 mL THF). The mixture was stirred for 3 hours and stripped to 25% of its volume (30-50 mL) and the precipitate was collected on a sintered glass funnel and rinsed with 3×40 mL of pentane to give 11.50 g (80% yield) of a pale yellow powder, 98% pure by $^1$H NMR. $^1$H NMR (benzene-$d_6$): δ 7.10 (d, 3.48, meta-Ar-H), δ 6.98 (t, 1.97, para-Ar-H), δ 4.83 (s, 1.00, backbone-C—H), and δ 1.71 (s, 5.32, $CH_3$). $^1$H NMR (acetonitrile-$d_3$): δ 7.37 (overlap, 5.57, meta-Ar-H and 0.4 eq. benzene), δ 6.98 (t, 1.98, para-Ar-H), δ 4.81 (s, 1.00, backbone-C—H), and δ 1.69 (s, 5.56, $CH_3$). Calculated elemental analysis: C, 48.30; H, 3.21; N, 5.28; experimental elemental analysis (average of three runs): C, 48.29; H, 3.07; N, 5.66.

Example 2

Synthesis and Characterization of [$Cl_2NN_{F6}$]Cu Catalyst

The [$Cl_2NN_{F6}$]Cu catalyst can be prepared as outlined below.

A. Preparation of 2,6-$Cl_2C_6H_3N_3$ ($Cl_2ArN_3$)—Following a literature procedure for the conversion of aromatic amines to azides (Barral, K.; Moorhouse, A. D.; Moses, J. E. *Org. Lett.* 2007, 9, 1809-1811), a solution of 2,6-dichloroaniline (6.41 g, 0.39.5 mmol) in 50 mL MeCN was cooled to 0° C. in an ice bath. Chilled (0° C.) tert-butylnitrite (6.10 g, 59.2 mmol) was added followed by chilled trimethylsilylazide (5.45 g, 47.4 mmol). The reaction mixture was allowed to stir for 3 hours at room temperature. The volatiles were removed in vacuo maintaining a temperature below 35° C. The resulting crude oil was purified via column chromatography using pentane and collecting the first yellow fraction to provide 67% yield (4.99 g; 26.5 mmol). $^1$H NMR (benzene-$d_6$): δ 6.689 (d, 2, m-Ar-H), 6.189 (t, 1, p-Ar-H); m/z (CI mode)= 161 ($M^+$-$N_2$).

B. Preparation of $Cl_2ArN$=$PMe_3$—Under a nitrogen atmosphere a chilled (−35° C.) solution of 2,6-dichlorophenylazide ($Cl_2ArN_3$) (4.99 g, 26.5 mmol) in 10 mL of THF was added slowly to a chilled (−35° C.) solution trimethylphosphine (26.5 mL of a 1.0 M solution in THF, 26.5 mmol). Rapid gas evolution was observed. The yellow solution was allowed to stand for 20 minutes at room temperature. All volatiles were removed from the crude product in vacuo. The product was used as is for the following steps. $^1$H NMR (benzene-$d_6$): δ 7.264 (d, 2, m-Ar-H), 6.333 (t, 1, p-Ar-H), 1.000 (s, 9, Me); m/z (CI mode)=237 ($M^+$).

C. Thermal Synthesis of H[$Cl_2NN_{F6}$]—An aza-Wittig reaction similar to that reported by Sadighi (Laitar, D. S.; Mathison, C. J. N.; Davis, W. M.; Sadighi, J. P. *Inorg. Chem* 2003, 42, 7354-7356) was used to prepare the new fluorinated β-diketiminate ligand H[$Cl_2NN_{F6}$]. Under a nitrogen atmosphere, $Cl_2ArN$=$PMe_3$ (0.458 g, 1.94 mmol) in 3 mL toluene and 1,1,1,5,5,5-heaxafluoropentadione (0.201 g, 0.966 mmol) in 3 mL of toluene were added together inside a glass pressure vessel. The pressure vessel was sealed and heated for 108 hours at 100° C. The brown reaction was concentrated to remove all volatiles. The brown remaining oil was purified via column chromatography using 30:1 hexane:toluene as the mobile phase. The first bright yellow fraction was collected. Crystallization from methanol at −20° C. afforded bright yellow crystals in 56% yield (269 mg; 0.543 mmol). $^1$H NMR (benzene-d$_6$): δ 11.50 (s, 1H, N—H) δ 6.83 (d, 4H, meta-Ar-H), δ 6.30 (t, 2H, para-Ar-H), δ 6.10 (s, 1, backbone-C—H); $^{13}$C NMR (benzene-d$_6$): δ 153.07, 152.76, 138.62, 131.18, 128.50, 127.98, 121.04, 118.19, 89.82; $^{19}$F NMR (C$_6$F$_6$ in C$_6$D$_6$): −69.7; m/z (CI mode)=497 (M$^+$).

D. Microwave Synthesis of H[Cl$_2$NN$_{F6}$]—Under a nitrogen atmosphere, Cl$_2$ArN=PMe$_3$ (0.620 g, 2.63 mmol) and 1,1,1,5,5,5-heaxafluoropentadione (0.273 g, 1.31 mmol) were added together in 4 mL toluene were inside a microwave pressure vessel. The microwave vessel was sealed. The microwave heated the reaction mixture for 5 hours at 150° C., 100 Watts, and 275 psi. All volatiles were removed from the crude product in vacuo. The crude product was purified via column chromatography using silica and hexanes:toluene (30:1) and a bright yellow oil was collected as the first compound off the column. Crystallization from pentane at −35° C. afforded bright yellow crystals in 42% yield (273 mg; 0.551 mmol). Characterization identical to the thermal synthesis of H[Cl$_2$NN$_{F6}$].

E. Preparation of [Cl$_2$NN$_{F6}$]Cu—Under a nitrogen atmosphere, H[Cl$_2$NN$_{F6}$] (2.38 g, 4.79 mmol) was added to a stirring solution of copper(I) tert-butoxide (0.786 g, 5.75 mmol) in benzene (6 mL) and pentane (10 mL). The reaction mixture was allowed to stir for 3 hours at room temperature. All volatiles were removed under vacuo and the remaining solid was washed with cold pentane to afford an orange solid in 75% yield (2.15 g; 1.79 mmol). $^1$H NMR (benzene-d$_6$): δ 6.993 (d, 4H, meta-Ar-H), δ 6.401 (t, 2H, para-Ar-H), δ 6.095 (s, 1.00, backbone-C—H); $^{19}$F NMR (C$_6$F$_6$ in C$_6$D$_6$): −67.5.

F. Preparation of [Cl$_2$NN$_{F6}$]CuOtBu—Under a nitrogen atmosphere, a chilled (−35° C.) solution tert-butylperoxide (0.141 g, 0.967 mmol) in 2 mL benzene was added to a chilled solution of [Cl$_2$NN$_{F6}$]Cu (taken as {[Cl$_2$NN$_{F6}$]Cu}$_2$(benzene): 0.135 g, 0.113 mmol) in 3 mL pentane. The reaction mixture was allowed to stir at room temperature for 90 minutes and changed color from orange/yellow to purple/maroon. All volatiles were removed under vacuo and the remaining solid was taken up in 20 mL of pentane and filtered through Celite® and concentrated for crystallization at −35° C. to afford red crystals in 34% yield (0.050 g, 0.0791 mmol). The product was characterized by single-crystal X-ray diffraction.

Example 3

Synthesis of [Cl$_2$NO$_2$NN]Cu Catalyst

Figure 1:
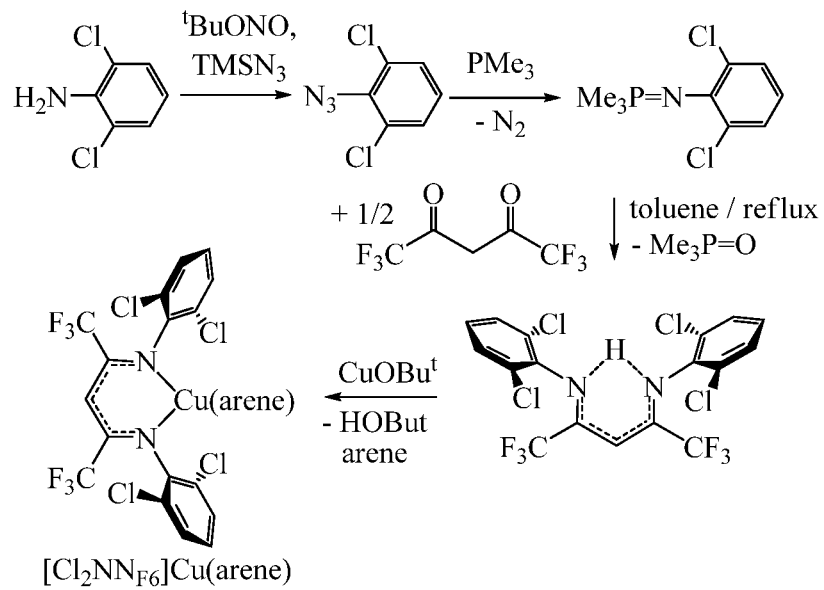
FIG. 1 depicts a scheme showing a synthetic route to β-diketiminates and β-diketiminato copper(I) complexes.
Figure 2:
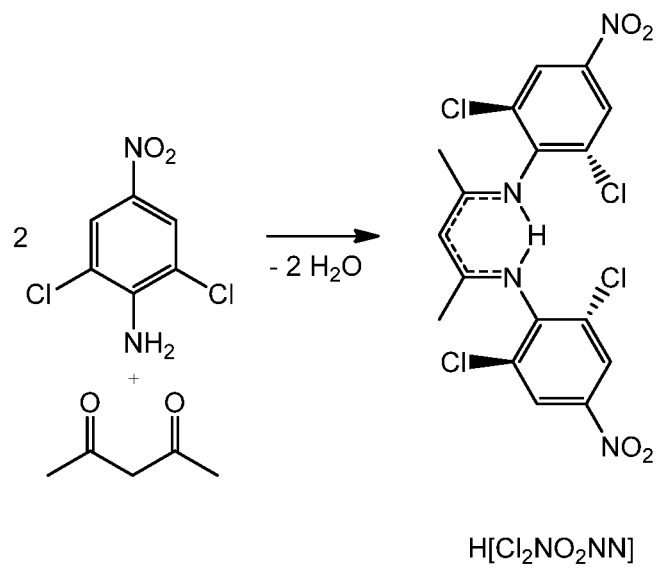
FIG. 2 depicts a scheme showing a synthetic route to $H[Cl_2NO_2NN]$.
Figure 3:
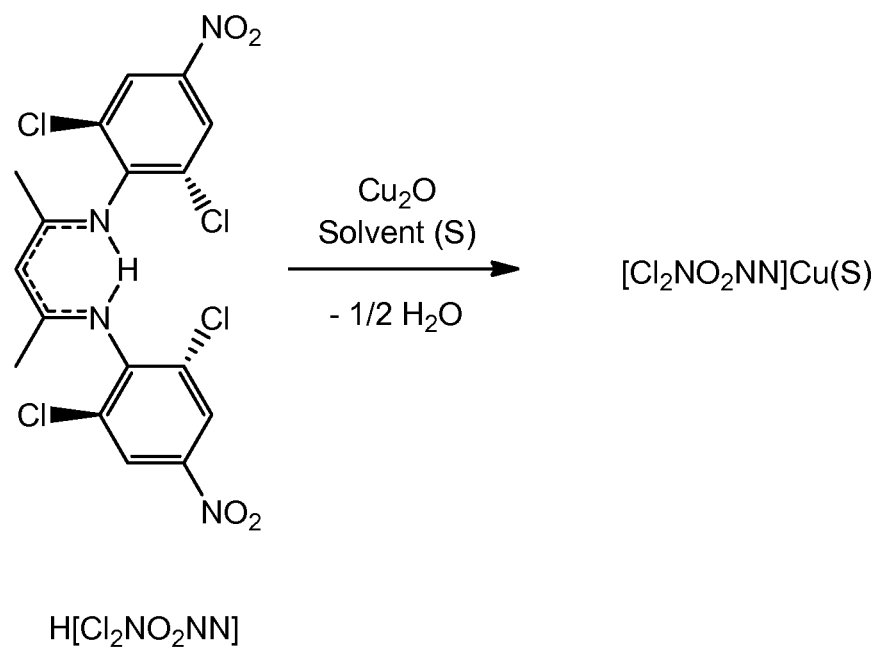
FIG. 3 depicts a scheme showing a synthetic route to $[Cl_2NO_2NN]Cu(S)$, where S denotes solvent.

The [Cl$_2$NO$_2$NN]Cu catalyst can be prepared as outlined in FIG. 2 and FIG. 3.

Example 4

Catalyst Stock Solution Preparation

A stock solution was prepared under inert atmosphere by dissolving {[Cl$_2$NN]Cu}$_2$(benzene) (486.94 mg, 0.500 mmol) in 20 mL of benzene to give a 0.05 M solution based on mononuclear [Cl$_2$NN]Cu.

1 mol % [Cl$_2$NN]Cu=0.01 mmol=0.200 mL catalyst solution
2.5 mol % [Cl$_2$NN]Cu=0.025 mmol=0.500 mL catalyst solution
5 mol % [Cl$_2$NN]Cu=0.05 mmol=1.00 mL catalyst solution
10 mol % [Cl$_2$NN]Cu=0.10 mmol=2.00 mL catalyst solution General Procedure for Examples 5-8

Use of Aliphatic Alcohols as Substrates

A catalyst stock solution of catalyst was prepared as in Example 4.

Reactions are described with using 1 mmol of 1-pentanol and 10 eq of the CH-substrate. The catalyst loading was 1 mol % and it was used 1.2 eq of the tert-butyl peroxide. The reactions were also done with 100 eq of the CH-substrate, different catalyst loadings (5 mol % and 10 mol %) and at 50° C. or room temperature.

Representative results are tabulated in FIG. 4.

Example 5

PhCH(OCH$_2$CH$_2$CH$_2$CH$_2$CH$_3$)Me

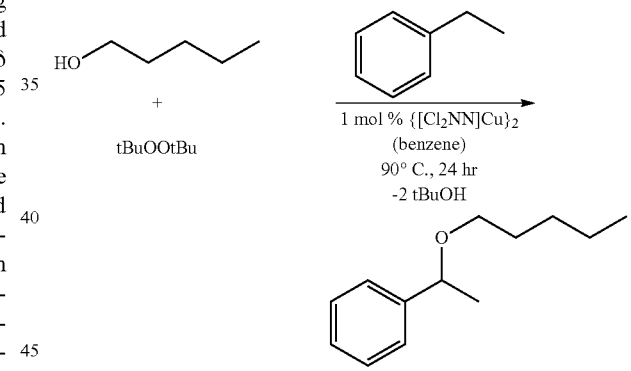

Into a pressure vessel 1-pentanol (109 μL, 1 mmol, 1 eq) was added and diluted with ethylbenzene (1.225 mL, 10 mmol, 10 eq). To this stirring solution was added 1 mol % of a stock solution of {[Cl$_2$NN]Cu}$_2$(benzene) from the catalyst stock solution described in Example 4 (200 μL=0.01 mmol). After adding of tert-butyl peroxide (220 μL, 1.2 mmol), the pressure vessel was sealed and heated to 90° C. for 24 hr. The catalyst was separated by exposing the mixture to air and filtering through Celite®. After removing ethyl benzene under vacuum, the residue was analyzed by GC/MS and $^1$H NMR to determine the yield and consumption of starting materials. $^1$H NMR Yield: 48%.

$^1$H NMR (400 MHz, CDCl$_3$): δ 7.27 (m, 5H, Ph-H), 4.38 (q, 1H, methine H), 3.78 (t, 2H, —O—CH$_2$—), 1.55 (m, 2H, —O—CH$_2$—CH$_2$—), 1.43 (d, 3H, Ph-CH$_2$—CH$_3$), 1.26 (m, 4H, —CH$_2$—CH$_2$—CH$_3$), 0.88 (t, 3H, —CH$_3$).

$^{13}$C {$^1$H} NMR (CDCl$_3$): δ=77.86 (Ph-CH(CH$_3$)O—), 68.76 (—O—CH$_2$—), 29.65 (—O—CH$_2$—CH$_2$—), 28.35

(—CH$_2$—CH$_2$—CH$_3$), 24.23 (Ph-CH(CH$_3$)O—), 22.52 (—CH$_2$—CH$_2$—CH$_3$), 14.01 (—CH$_3$).

GC/MS=Fragment Ions m/z=176.9 [M-15] and m/z=105 [M-87] (EI mode).

The spectroscopic data was in agreement with previously published data. Ke, F. et al. (2011) *Tetrahedron Letters* 52:318-320.

Example 6

c-C$_6$H$_{11}$—OCH$_2$CH$_2$CH$_2$CH$_2$CH$_3$

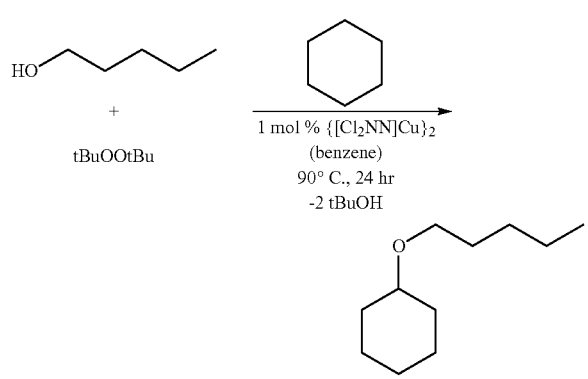

Into a pressure vessel 1-pentanol (109 μL, 1 mmol, 1 eq) was added and diluted with cyclohexane (1.080 mL, 10 mmol, 10 eq). To this stirring solution was added 1 mol % of a stock solution of {[Cl$_2$NN]Cu}$_2$(benzene) from the catalyst stock solution described in Example 4 (200 μL=0.01 mmol). After adding of tert-butyl peroxide (220 μL, 1.2 mmol), the pressure vessel was sealed and heated to 90° C. for 24 hr. The catalyst was separated by exposing the mixture to air and filtering through Celite®. After removing cyclohexane under vacuum, the residue was analyzed by $^1$H NMR and GC/MS to determine the yield and consumption of starting materials. $^1$H NMR Yield: 40%.

$^1$H NMR (400 MHz, CDCl$_3$): δ=3.19 (m, 1H, HC—O—CH$_2$—).

GC/MS m/z=170.1 (EI mode).

Example 7

PhCH$_2$OCH$_2$CH$_2$CH$_2$CH$_2$CH$_3$

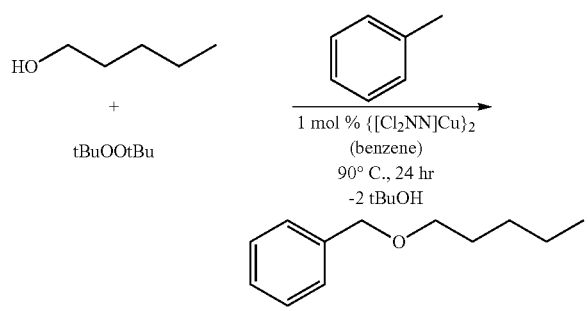

Into a pressure vessel 1-pentanol (109 μL, 1 mmol, 1 eq) was added and diluted with toluene (1.063 mL, 10 mmol, 10 eq). To this stirring solution was added 1 mol % of a stock solution of {[Cl$_2$NN]Cu}$_2$(benzene) from the catalyst stock solution described in Example 4 (200 μL=0.01 mmol). After adding of tert-butyl peroxide (220 μL, 1.2 mmol), the pressure vessel was sealed and heated to 90° C. for 24 hr. The catalyst was separated by exposing the mixture to air and filtering through Celite®. After removing toluene under vacuum, the residue was analyzed by $^1$H NMR and GC/MS to determine the yield and consumption of starting materials. $^1$H NMR Yield: 20%.

$^1$H NMR (400 MHz, CDCl$_3$): δ=7.21 (m, 5, Ph-H), 4.51 (s, 2H, Ph-CH$_2$—O—), 3.47 (t, 2H, —O—CH$_2$), 1.61 (m, 2H, —O—CH$_2$—CH$_2$—), 1.34 (m, 4H, —CH$_2$—CH$_2$—CH$_3$), 0.91 (m, 3H, —CH$_3$).

$^{13}$C {$^1$H} NMR (CDCl$_3$): δ=72.91 (Ph-CH$_2$—O—), 70.63 (—O—CH$_2$—), 29.60 (—O—CH$_2$—CH$_2$—), 28.54 (—CH$_2$—CH$_2$—CH$_3$), 22.52 (—CH$_2$—CH$_2$—CH$_3$), 14.10 (—CH$_3$).

GC/MS m/z=177.1 (EI mode).

The spectroscopic data was in agreement with previously published data. Nishiyama, T. et al. (1999) *Can. J. Chem.* 77:258-262.

Example 8

3-cyclohexenyl-OCH$_2$CH$_2$CH$_2$CH$_2$CH$_3$

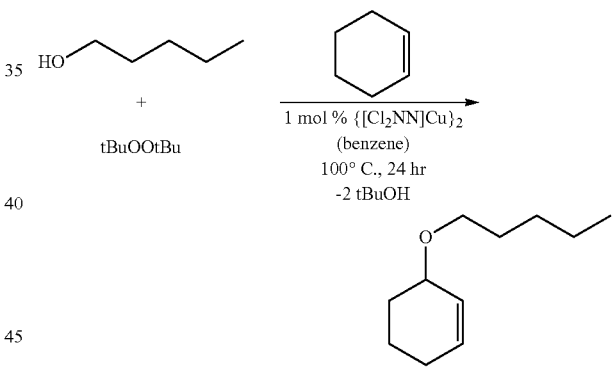

Into a pressure vessel 1-pentanol (109 μL, 1 mmol, 1 eq) was added and diluted with cyclohexene (1.01 mL, 10 mmol, 10 eq). To this stirring solution was added 1 mol % of a stock solution of {[Cl$_2$NN]Cu}$_2$(benzene) from the catalyst stock solution described in Example 4 (200 μL=0.01 mmol). After adding of tert-butyl peroxide (220 μL, 1.2 mmol), the pressure vessel was sealed and heated to 100° C. for 24 hr. The catalyst was separated by exposing the mixture to air and filtering through Celite®. After removing cyclohexene under vacuum, the residue was analyzed by $^1$H NMR and GC/MS to determine the yield and consumption of starting materials. $^1$H NMR Yield: 46%.

$^1$H NMR (400 MHz, CDCl$_3$, partial): 3.82 (m, 1H, HC—O—CH$_2$—).

GC/MS m/z=168.0 (EI mode).

The spectroscopic data was in agreement with previously published data. Móller, K. C. et al. (1997) *Electrochimica Acta.* 42:1971-1978.

Example 9 c-C$_6$H$_{11}$—O$^t$Bu

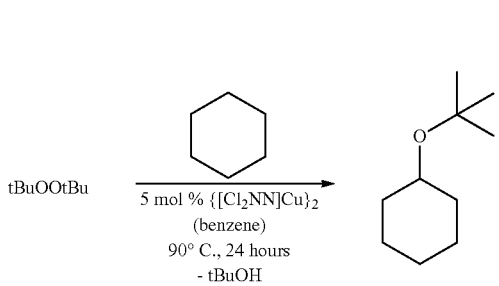

Into a pressure vessel cyclohexane (15 mL) was added. To this stirring solution was added 5 mol % of a stock solution of {[Cl$_2$NN]Cu}$_2$(benzene) from the catalyst stock solution described in Example 4 (1.00 mL=0.05 mmol). After adding of tert-butyl peroxide (220 μL, 1.2 mmol), the pressure vessel was sealed and heated to 90° C. for 24 hr. The catalyst was separated by exposing the mixture to air and filtering through Celite®. After removing cyclohexane under vacuum, the residue was analyzed by $^1$H NMR and GC/MS to determine the yield and consumption of starting materials. $^1$H NMR yield: 50%.

$^1$H NMR (400 MHz, CDCl$_3$, partial): δ=3.32 (m, 1H, HCO$^t$Bu).

GC/MS fragment ion m/z=140.5 [M-15] (EI mode).

The spectroscopic data was in agreement with previously published data. Kleinpeter, E. et al. (2007) *Tetrahedron.* 63:9071-9081.

Examples 10-14

Use of Acetyl-Protected Phenols as Substrates

A catalyst stock solution of catalyst was prepared as in Example 4.

Reactions are described with using 1 mmol of the phenyl acetate and 10 eq of the CH-substrate. The catalyst loading is 1 mol % and it was used 1.2 eq of the tert-butyl peroxide. The reactions were also done with 5 eq of the CH-substrate, different catalyst loadings (2.5 mol % and 5 mol %) and at room temperature.

Representative results are tabulated in FIG. 5.

Example 10

α-Phenoxyethylbenzene

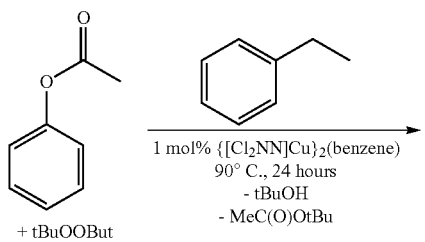

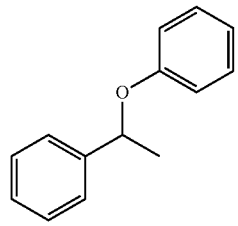

Into a pressure vessel phenyl acetate (126 μL, 1 mmol, 1 eq) was added and diluted with ethylbenzene (1.220 mL, 10 mmol, 10 eq). To this stirring solution was added 1 mol % of a stock solution of {[Cl$_2$NN]Cu}$_2$(benzene) from the catalyst stock solution described in Example 4 (200 μL=0.01 mmol). After adding of tert-butyl peroxide (220 μL, 1.2 mmol), the pressure vessel was sealed and heated to 90° C. for 24 hr. The catalyst was separated by exposing the mixture to air and filtering through Celite®. After removing ethyl benzene under vacuum, the residue was analyzed by GC/MS to determine the yield and consumption of starting materials.

$^1$H NMR (400 MHz, CDCl$_3$, partial): δ=5.31 (q, 1H, Ph-CH(CH$_3$)OPh), 1.64-1.63 (d, 3H, Ph-CH(CH$_3$)OPh.

GC/MS m/z=183 [M-15], 105 [M-93] (EI mode).

The spectroscopic data was in agreement with previously published data. Utsunomiya, M. et al. (2003) *Angew. Chem. Int. Ed.* 42:5865-5868.

Example 11

Cyclohexyl Phenyl Ether

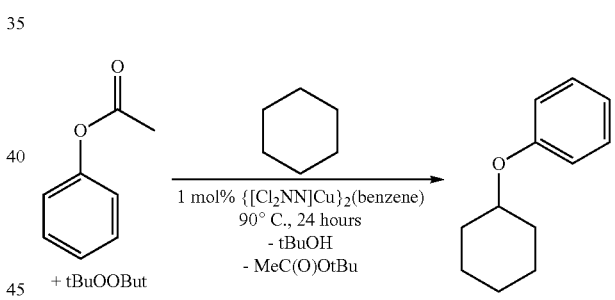

Into a pressure vessel phenyl acetate (126 μL, 1 mmol, 1 eq) was added and diluted with cyclohexane (1.080 mL, 10 mmol, 10 eq). To this stirring solution was added 1 mol % of a stock solution of {[Cl$_2$NN]Cu}$_2$(benzene) from the catalyst stock solution described in Example 4 (200 μL=0.01 mmol). After adding of tert-butyl peroxide (220 μL, 1.2 mmol), the pressure vessel was sealed and heated to 90° C. for 24 hr. The catalyst was separated by exposing the mixture to air and filtering through Celite®. After removing cyclohexane under vacuum, the residue was analyzed by $^1$H NMR and GC/MS to determine the yield and consumption of starting materials.

$^1$H NMR (CDCl$_3$): δ 7.25 (t, 2, o-Ph-H), δ 6.91 (t, 2, m-Ph-H), δ 6.89 (d, 1, p-Ph-H), δ 4.23 (hept, 1, H—CO—Ar), δ 1.98 (m, 1, CH$_2$), δ 1.80 (m, 1, CH$_2$), δ 1.53 (m, 2, CH$_2$), δ 1.35 (m, 2, CH$_2$).

$^{13}$C {$^1$H} NMR (CDCl$_3$): δ 157.75 (i-Ph), δ 129.37 (o-Ph), δ 120.43 (m-Ph), δ 116.05 (p-Ph), δ 75.33 (i-CH), δ 31.85 (o-CH$_2$), δ 25.64 (p-CH$_2$), δ 23.81 (m-CH$_2$).

$^1$H,$^{13}$C-gHSQC (CDCl$_3$): δ($^1$H)/δ($^{13}$C)=7.25/129.37 (o-Ph); 6.91/120.43 (m-Ph); 6.89/116.05 (p-Ph); 4.23/75.33

(H—CO—Ar); 1.98, 1.53/31.85 (o-CH$_2$); 1.80, 1.35/23.81 (m-CH$_2$); 1.60, 1.30/25.64 (o-CH$_2$).

$^1$H,$^1$H-gCOSY (CDCl$_3$): δ($^1$H)/δ($^1$H)=7.25/6.91/6.89 (o-Ph/m-Ph/p-Ph), 4.23/1.98/1.53 (H—CO—Ar/o-CH$_2$), 1.80/1.60/1.35 (m-CH$_2$/p-CH$_2$/m-CH$_2$).

GC/MS m/z=176.8 (CI mode).

The spectroscopic data was in agreement with previously published data. Rosenfeld, D. C. et al. (2006) *Org. Lett.* 8:4179-4182.

Example 12

Pentyl Phenyl Ethers

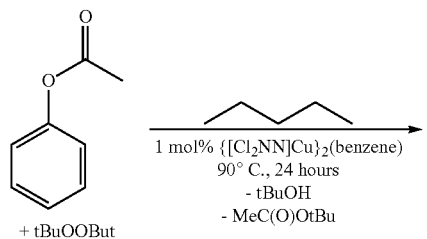

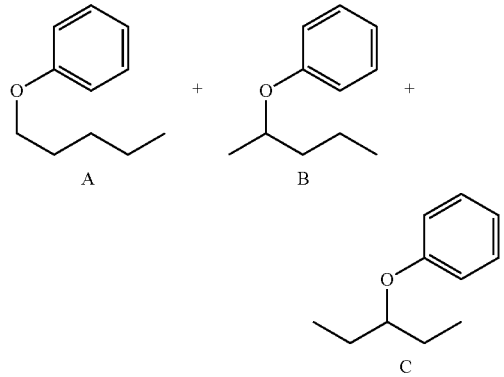

Into a pressure vessel phenyl acetate (126 μL, 1 mmol, 1 eq) was added and diluted with n-pentane (1.145 mL, 10 mmol, 10 eq). To this stirring solution was added 1 mol % of a stock solution of {[Cl$_2$NN]Cu}$_2$(benzene) from the catalyst stock solution described in Example 4 (200 μL=0.01 mmol). After adding of tert-butyl peroxide (220 μL, 1.2 mmol), the pressure vessel was sealed and heated to 90° C. for 24 hr. The catalyst was separated by exposing the mixture to air and filtering through Celite®. After removing pentane under vacuum, the residue was analyzed by GC/MS to determine the yield and consumption of starting materials.

$^1$H NMR (400 MHz, CDCl$_3$, partial): δ 4.34 (B, sextet, 1, CH$_2$CH(OPh)CH$_3$), 4.09 (C, quintet, 1, CH$_2$CH(OPh)CH$_2$), 3.94 (A, CH$_2$CH$_2$OPh).

NMR revealed yields of products A (4%), B (24%), C (11%).

GC/MS m/z=163.5 (EI mode; three different isomers).

Example 13 c-C$_6$H$_{11}$—OPh

Via Phenyl Trifluoroacetate

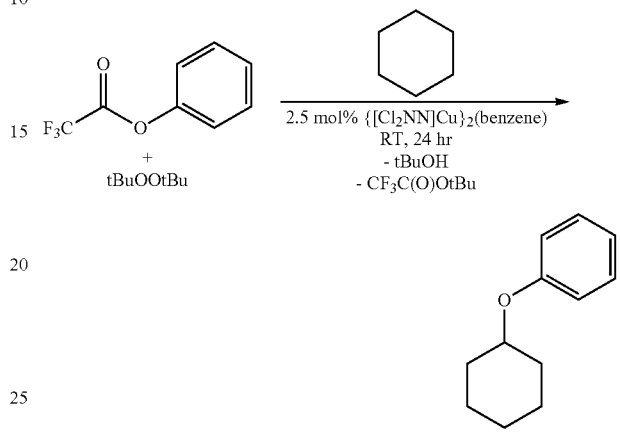

Into a screw cap vial phenyl trifluoroacetate (149 μL, 1 mmol, 1 eq) was added and diluted with cyclohexane (1.080 mL, 10 mmol, 10 eq). To this stirring solution was added 2.5 mol % of a stock solution of {[Cl$_2$NN]Cu}$_2$(benzene) from the catalyst stock solution described in Example 4 (500 μL=0.025 mmol). After adding of tert-butyl peroxide (220 μL, 1.2 mmol), the vial was sealed and left to stir for 24 hr. The catalyst was separated by exposing the mixture to air and filtering through Celite®. After removing cyclohexane under vacuum, the residue was analyzed by $^1$H NMR and GC/MS to determine the yield and consumption of starting materials. $^1$H NMR Yield: 12%.

$^1$H NMR (400 MHz, CDCl$_3$, partial): δ=4.24 (m, 1H, HCO-Ph).

GC/MS m/z=176.0 (EI mode).

The spectroscopic data was in agreement with previously published data. Rosenfeld, D. C. et al. (2006) *Org. Lett.* 8:4179-4182.

Example 14

PhCH(OPh)Me

Via Phenyl Trifluoroacetate

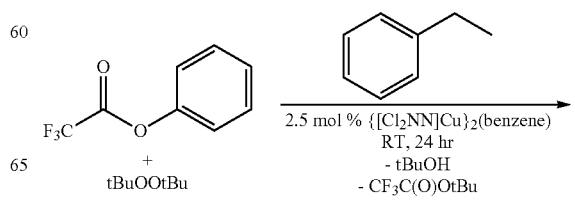

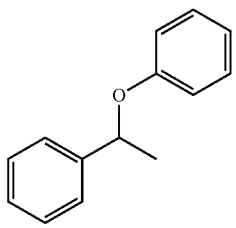

Into a screw cap vial phenyl trifluoroacetate (149 μL, 1 mmol, 1 eq) was added and diluted with ethylbenzene (1.225 mL, 10 mmol, 10 eq). To this stirring solution was added 2.5 mol % of a stock solution of {[Cl$_2$NN]Cu}$_2$(benzene) from the catalyst stock solution described in Example 4 (500 μL=0.025 mmol). After adding of tert-butyl peroxide (220 μL, 1.2 mmol), the vial was sealed and left to stir for 24 hr. The catalyst was separated by exposing the mixture to air and filtering through Celite®. After removing ethylbenzene under vacuum, the residue was analyzed by $^1$H NMR and GC/MS to determine the yield and consumption of starting materials. $^1$H NMR Yield: 7%.

$^1$H NMR (400 MHz, CDCl$_3$, partial): δ=5.31 (q, 1H, Ph-CH(CH$_3$)OPh), 1.64-1.63 (d, 3H, Ph-CH(CH$_3$)OPh.

GC/MS m/z=183 [M-15], 105 [M-93] (EI mode).

The spectroscopic data was in agreement with previously published data. Shintou, T. et al. (2004) *J. Am. Chem. Soc.* 126:7359-7367.

Examples 15-18

Use of Thioacetates and Disulfides as Reagents for C—S Bond Formation

Example 15

PhCH(SPh)Me

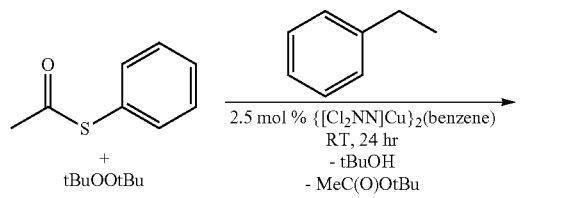

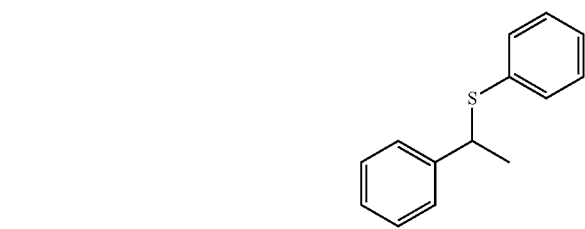

Into a screw cap vial S-phenyl thioacetate (135 μL, 1 mmol, 1 eq) was added and diluted with ethylbenzene (1.225 mL, 10 mmol, 10 eq). To this stirring solution was added 2.5 mol % of a stock solution of {[Cl$_2$NN]Cu}$_2$(benzene) from the catalyst stock solution described in Example 4 (500 μL=0.025 mmol). After adding of tert-butyl peroxide (220 μL, 1.2 mmol), the vial was sealed and left to stir for 24 hr. The catalyst was separated by exposing the mixture to air and filtering through Celite®. After removing ethylbenzene under vacuum, the residue was analyzed by $^1$H NMR and GC/MS to determine the yield and consumption of starting materials. $^1$H NMR yield: 38%.

$^1$H NMR (400 MHz, CDCl$_3$, partial): δ 4.34 (q, 1H, Ph-CH(CH$_3$)SPh), 1.63 (d, 3H, Ph-CH(CH$_3$)SPh.

GC/MS m/z=213.8 (EI mode).

The spectroscopic data was in agreement with previously published data. Sakai, N. et al. (2009) *Eur. J. Org. Chem.* 4123-4127; Miller, K. J. et al. (2003) *Eur. J. Org. Chem.* 1294-1299.

Example 16

1-cyclohexyl-SPh

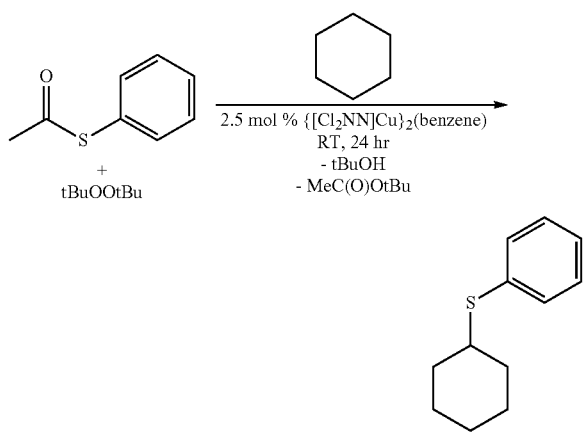

Into a screw cap vial S-phenyl thioacetate (135 μL, 1 mmol, 1 eq) was added and diluted with cyclohexane (1.080 mL, 10 mmol, 10 eq). To this stirring solution was added 2.5 mol % of a stock solution of {[Cl$_2$NN]Cu}$_2$(benzene) from the catalyst stock solution described in Example 4 (500 μL=0.025 mmol). After adding of tert-butyl peroxide (220 μL, 1.2 mmol), the vial was sealed and left to stir for 24 hr. The catalyst was separated by exposing the mixture to air and filtering through Celite®. After removing cyclohexane under vacuum, the residue was analyzed by $^1$H NMR and GC/MS to determine the yield and consumption of starting materials. $^1$H NMR yield: 20%.

$^1$H NMR (400 MHz, CDCl$_3$, partial): δ 3.11 (m, 1H, (CH—S-Ph).

GC/MS m/z=153.0 (EI mode).

The spectroscopic data was in agreement with previously published data. Bryliakov, K. P. et al. (2011) *Eur. J. Org Chem.* 4693-4698; Akkilagunta, V. K. et al. (2011) *J. Org. Chem.* 76:6819-6824.

Example 17

PhCH(S-2-py)Me

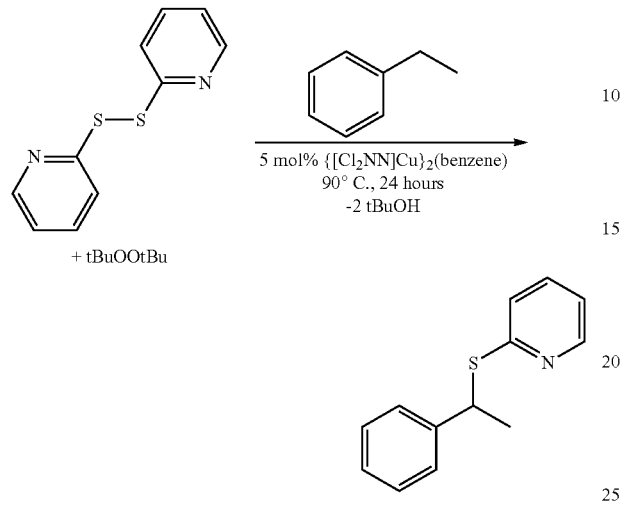

Into a pressure vessel 2,2'-dithiopyridine (0.220 g, 1 mmol, 1 eq) was added and diluted with ethylbenzene (1.225 mL, 10 mmol 10 eq). To this stirring solution was added 5 mol % of a stock solution of $\{[Cl_2NN]Cu\}_2$(benzene) from the catalyst stock solution described in Example 4 (1.00 mL=0.05 mmol). After adding of tert-butyl peroxide (220 μL, 1.2 mmol), the pressure vessel was sealed and heated to 90° C. for 24 hr. The catalyst was separated by exposing the mixture to air and filtering through Celite®. After removing ethylbenzene under vacuum, the residue was analyzed by $^1$H NMR and GC/MS to determine the yield and consumption of starting materials. $^1$H NMR yield: 25%.

$^1$H NMR (400 MHz, CDCl$_3$, partial): 5.11-5.10 (q, 1H, Ph-CH(CH$_3$)SPy), 1.64-1.63 (d, 3H, Ph-CH(CH$_3$)SPy.

GC/MS m/z=215.1 (EI mode).

The spectroscopic data was in agreement with previously published data. Nakamura, S. et al. (2000) *J. Am. Chem. Soc.* 122:11340-11347.

Example 18

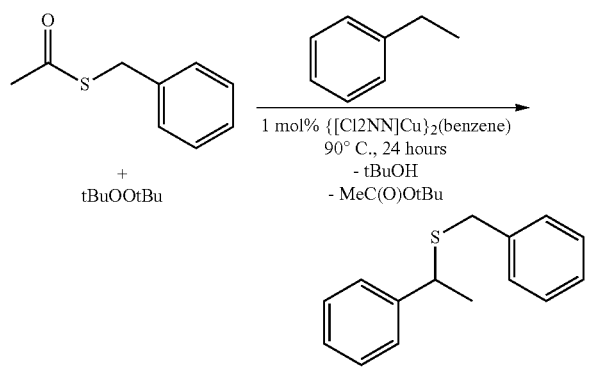

Into a pressure vessel S-benzyl ethanethioate (0.166 g, 1 mmol, 1 eq) was added and diluted with ethylbenzene (1.225 mL, 10 mmol, 10 eq). To this stirring solution was added 1 mol % of a stock solution of $\{[Cl_2NN]Cu\}_2$(benzene) from the catalyst stock solution described in Example 4 (200 μL=0.01 mmol). After adding of tert-butyl peroxide (220 μL, 1.2 mmol), the pressure vessel was sealed and heated to 90° C. for 24 hr. The catalyst was separated by exposing the mixture to air and filtering through Celite®. After removing ethylbenzene under vacuum, the residue was analyzed by $^1$H NMR and GC/MS to determine the yield and consumption of starting materials. $^1$H NMR Yield: 68%.

$^1$H NMR (400 MHz, CDCl$_3$, partial): δ=3.81 (q, 1H, PhCH(CH$_3$)SCH$_2$—)

GC/MS m/z=228 and m/z=105 [M-123] (EI mode)

The spectroscopic data was in agreement with previously published data. Miller, K. et al. (2003) *Eur. J. Org. Chem.* 1294-1299.

Examples 19-23

Use of Aliphatic Alcohols as Substrates

A catalyst stock solution of catalyst was prepared as in Example 4.

Reactions are described with using 1 mmol of an aliphatic alcohol and 10 eq of the CH-substrate. The catalyst loading was 1 mol % and it was used 1.2 eq of the tert-butyl peroxide. The reactions were also done with 100 eq of the CH-substrate, different catalyst loadings (5 mol % and 10 mol %) and at 50° C. or room temperature.

Figure 11:
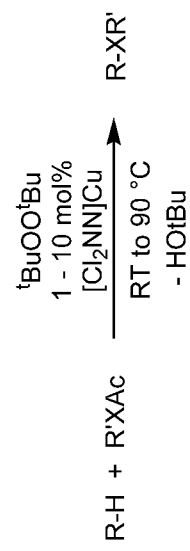
FIG. 11 is a table showing results of representative reactions using various alcohols and C—H substrates to form ethers and thioethers.

Representative results are tabulated in FIG. 11.

Example 19

PhCH(OCH$_3$)Me

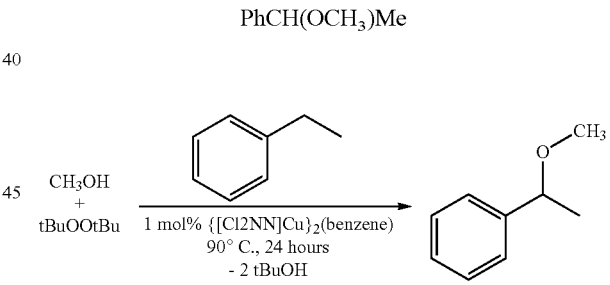

Into a pressure vessel methanol (84 μL, 1 mmol, 1 eq) was added and diluted with ethylbenzene (1.225 mL, 10 mmol, 10 eq). To this stirring solution was added 1 mol % of a stock solution of $\{[Cl_2NN]Cu\}_2$(benzene) from the catalyst stock solution described in Example 4 (200 μL=0.01 mmol). After adding of tert-butyl peroxide (220 μL, 1.2 mmol), the pressure vessel was sealed and heated to 90° C. for 24 hr. The catalyst was separated by exposing the mixture to air and filtering through Celite®. After removing ethylbenzene under vacuum, the residue was analyzed by GC/MS and $^1$H NMR to determine the yield and consumption of starting materials. $^1$H NMR Yield: 35%.

$^1$H NMR (400 MHz, CDCl$_3$, partial): 4.30 (q, 1H, PhCH(CH$_3$)OCH$_3$)

GC/MS=Fragment Ions m/z=121 [M-15] and m/z=105 [M-31] (EI mode)

The spectroscopic data was in agreement with previously published data. Ke, F. et al. (2011) *Tetrahedron Letters* 52:318-320.

Example 20

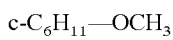

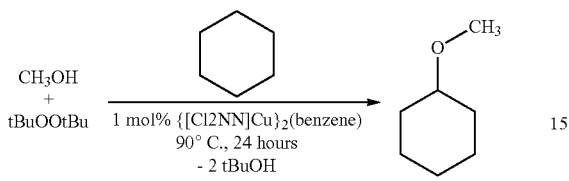

Into a pressure vessel methanol (84 μL, 1 mmol, 1 eq) was added and diluted with cyclohexane (1.080 mL, 10 mmol, 10 eq). To this stirring solution was added 1 mol % of a stock solution of {[Cl$_2$NN]Cu}$_2$(benzene) from the catalyst stock solution described in Example 4 (200 μL=0.01 mmol). After adding of tert-butyl peroxide (220 μL, 1.2 mmol), the pressure vessel was sealed and heated to 90° C. for 24 hr. The catalyst was separated by exposing the mixture to air and filtering through Celite®. After removing cyclohexane under vacuum, the residue was analyzed by $^1$H NMR and GC/MS to determine the yield and consumption of starting materials. $^1$H NMR Yield: 44%.

$^1$H NMR (400 MHz, CDCl$_3$, partial): δ=3.14 (m, 1H, HC—O—CH$_3$).

GC/MS m/z=114 (EI mode)

The spectroscopic data was in agreement with previously published data. Wang, D. et al. (2009) *Tetrahedron Letters* 50: 1282-1285.

Example 21

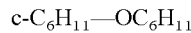

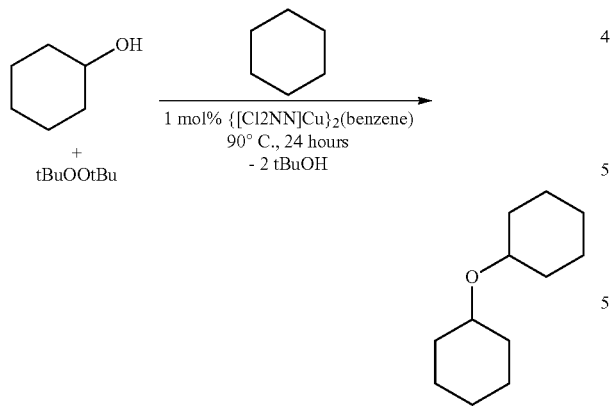

Into a pressure vessel cyclohexanol (0.100 g, 1 mmol, 1 eq) was added and diluted with cyclohexane (1.080 mL, 10 mmol, 10 eq). To this stirring solution was added 1 mol % of a stock solution of {[Cl$_2$NN]Cu}$_2$(benzene) from the catalyst stock solution described in Example 4 (200 μL=0.01 mmol). After adding of tert-butyl peroxide (220 μL, 1.2 mmol), the pressure vessel was sealed and heated to 90° C. for 24 hr. The catalyst was separated by exposing the mixture to air and filtering through Celite®. After removing cyclohexane under vacuum, the residue was analyzed by $^1$H NMR and GC/MS to determine the yield and consumption of starting materials. $^1$H NMR Yield: 37%.

$^1$H NMR (400 MHz, CDCl$_3$, partial): δ=3.31 (m, 2H, —HC—O—CH$_3$) GC/MS m/z=182 (EI mode)

The spectroscopic data was in agreement with previously published data. Zhang, Y. et al. (2012) *Tetrahedron*. 68: 7400-7407.

Example 22

PhCH(OCH$_2$CH$_2$CH$_2$CH$_2$CH$_2$CH$_2$CH$_2$CH$_3$)Me

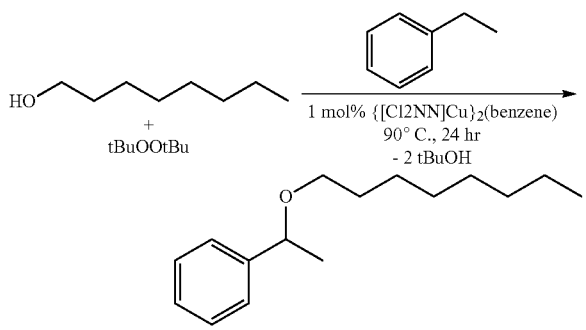

Into a pressure vessel 1-octanol (160 μL, 1 mmol, 1 eq) was added and diluted with ethylbenzene (1.225 mL, 10 mmol, 10 eq). To this stirring solution was added 1 mol % of a stock solution of {[Cl$_2$NN]Cu}$_2$(benzene) from the catalyst stock solution described in Example 4 (200 μL=0.01 mmol). After adding of tert-butyl peroxide (220 μL, 1.2 mmol), the pressure vessel was sealed and heated to 90° C. for 24 hr. The catalyst was separated by exposing the mixture to air and filtering through Celite®. After removing ethylbenzene under vacuum, the residue was analyzed by $^1$H NMR and GC/MS to determine the yield and consumption of starting materials. $^1$H NMR Yield: 52%.

$^1$H NMR (400 MHz, CDCl$_3$, partial): δ=4.39 (q, 1H, PhCH(CH$_3$)OCH$_2$—) GC/MS m/z=219 [M-15] and m/z=105 [M-129] (EI mode)

The spectroscopic data was in agreement with previously published data. Fujii, Y. et al. (2005) *Bull. Chem. Soc. Jpn.* 78: 456-463.

Example 23 c-C$_6$H$_{11}$—OCH$_2$CH$_2$CH$_2$CH$_2$CH$_2$CH$_2$CH$_2$CH$_3$

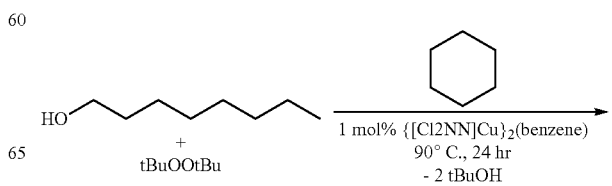

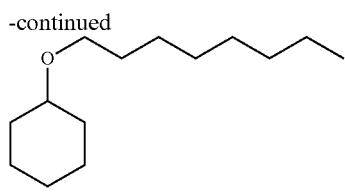

Into a pressure vessel 1-octanol (160 μL, 1 mmol, 1 eq) was added and diluted with cyclohexane (1.080 mL, 10 mmol, 10 eq). To this stirring solution was added 1 mol % of a stock solution of {[Cl$_2$NN]Cu}$_2$(benzene) from the catalyst stock solution described in Example 4 (200 μL=0.01 mmol). After adding of tert-butyl peroxide (220 μL, 1.2 mmol), the pressure vessel was sealed and heated to 90° C. for 24 hr. The catalyst was separated by exposing the mixture to air and filtering through Celite®. After removing cyclohexane under vacuum, the residue was analyzed by $^1$H NMR and GC/MS to determine the yield and consumption of starting materials. $^1$H NMR Yield: 42%.

$^1$H NMR (400 MHz, CDCl$_3$, partial): δ=3.19 (m, 1H, —HC—O—CH$_2$—)

GC/MS m/z=212 and m/z=83 [M-129] (EI mode)

The spectroscopic data was in agreement with previously published data. Gellert, B. et al. (2011) Chem. Eur. J. 17: 12203-12209.

Example 24

Mechanistic Considerations

Kinetic analysis of the reaction of the copper(I)β-diketiminate [Cl$_2$NN]Cu ([Cu$^I$]) with tBuOOtBu to give [Cu$^{II}$]-OtBu (1) reveals first-order behavior in each component implicating the formation of free tBuO. radicals. Added pyridine mildly inhibits this reaction, indicating competition between tBuOOtBu and pyridine for coordination at [Cu$^I$] prior to peroxide activation. Reaction of [Cu$^I$] with dicumyl peroxide leads to [Cu$^{II}$]-OCMe$_2$Ph (3) and acetophenone suggesting the intermediacy of the PhMe$_2$CO. radical. Computational methods provide insight into the activation of tBuOOtBu at [Cu$^I$]. The novel peroxide adduct [Cu$^I$](tBuOOtBu) (4) and the square planar [Cu$^{III}$](OtBu)$_2$ (5) were identified, each unstable toward loss of the tBuO. radical. Facile generation of the tBuO. radical is harnessed in the catalytic C—H etherification of cyclohexane with tBuOOtBu at rt employing [Cu$^I$] (5 mol %) to give the ether Cy-OtBu in 60% yield.

To better understand the activation and roles of tBuOOtBu in this and other Cu-based C—H functionalization systems, we undertook an integrated experimental-theoretical investigation involving the reaction between tBuOOtBu and [CuI]. Addition of 20 equiv of tBuOOtBu to [Cu$^I$] (initially 0.50 mM) in fluorobenzene over −20 to +20° C. results in rapid, quantitative conversion to [Cu$^{II}$]-OtBu (1), which has a strong optical band at λ$_{max}$=481 nm (ε=3560 M$^{-1}$ cm$^{-1}$). To avoid photochemical dissociation of tBuOOtBu (optically silent above λ=350 nm), we followed the reactions at a single wavelength (λ=481 nm) in an otherwise dark environment. In each case, first-order growth of 1 takes place affording the pseudo-first-order rate constant k$_{obs}$. The linear plot of k$_{obs}$ vs. [tBuOOtBu] at 10° C. indicates a second-order overall rate law: rate=k[Cu$^I$][tBuOOtBu].

Figure 7:
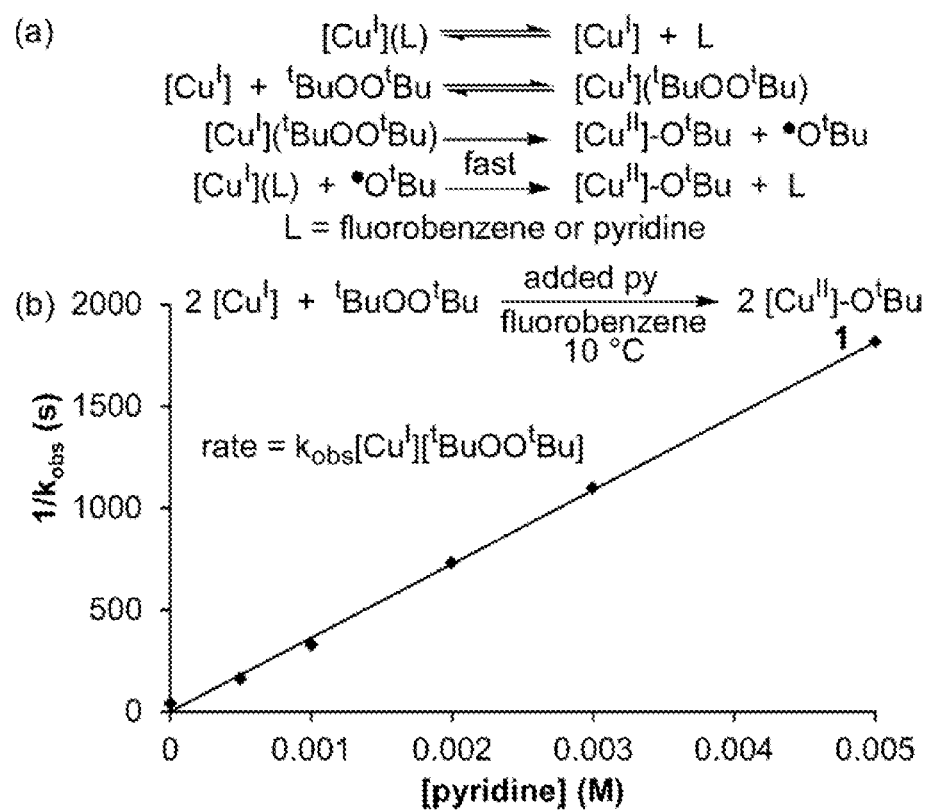
FIG. 7 is (a) mechanistic and (b) kinetic analysis of oxidation of $[Cu^I]$ by tBuOOtBu in the presence of pyridine.

Second-order rate constants for the oxidation of [Cu$^I$] by tBuOOtBu in fluorobenzene span 0.13(2) to 5.9(2) M$^{-1}$ s$^{-1}$ over the temperature range −20 to +20° C. corresponding to activation parameters ΔH‡=13.6(4) kcal/mol and ΔS‡=8.3 (1.4) e.u. with ΔG‡ (298 K)=16.1(5) kcal/mol. The near-zero entropy of activation in this bimolecular reaction supports a role for fluorobenzene dissociation from [Cu$^I$] preceding the activation of tBuOOtBu that results in the formation of 1 and tBuO. The tert-butoxy radical is presumably rapidly captured by [Cu$^I$] in solution to form another equivalent of [Cu$^{II}$]-OtBu (FIG. 7(a), L=fluorobenzene).

To probe the requirement for ligand dissociation from [Cu$^I$] prior to interaction with tBuOOtBu (FIG. 7(b)), kinetic studies were performed with varying amounts of pyridine, which binds reversibly to the [Cu$^I$] fragment. Addition of excess pyridine to {[Cu$^I$]}$_2$(μ-benzene) in ether allows for isolation and crystallization of [CuI](py) (2). The X-ray structure of 2 is similar to those of related β-diketiminato Cu(I) pyridine adducts such as [Me$_2$NN]Cu(2,4-lutidine). Based on the shoulder at x=416 nm in the UV-vis spectrum of [Cu$^I$] (py), which is absent in [CuI](η$^2$-C$_6$H$_5$F), we obtained thermodynamic parameters ΔH=−0.6(1) kcal/mol, ΔS=1.3(1) e.u. with ΔG$_{298}$=−0.9(1) kcal/mol for binding of pyridine, which includes loss of fluorobenzene. Addition of pyridine (1-10 equiv) at 10° C. slows the first-order growth of [Cu$^{II}$]-OtBu in the reaction of [Cu$^I$] (initially 0.50 mM) and tBuOOtBu (20 equiv) (FIG. 7(a), L=pyridine). A plot of 1/k$_{obs}$ vs [pyridine] gives a straight line (FIG. 7(b)) indicating an inverse first-order dependence on pyridine. The presence of 10 equiv of pyridine leads to a 47-fold reduction in rate as compared to comparable pyridine-free conditions. These observations signal the importance of pyridine dissociation from [Cu$^I$] during reaction with tBuOOtBu (FIG. 7(a)). We note that pyridine also binds to the copper(II) alkoxide [Cu$^{II}$]-OtBu, albeit weakly, shown by a shift in the optical band of 3 at 481 nm that moves to 496 nm with excess pyridine (40 equiv and more) accompanied by a reduction in intensity.

Figure 8:
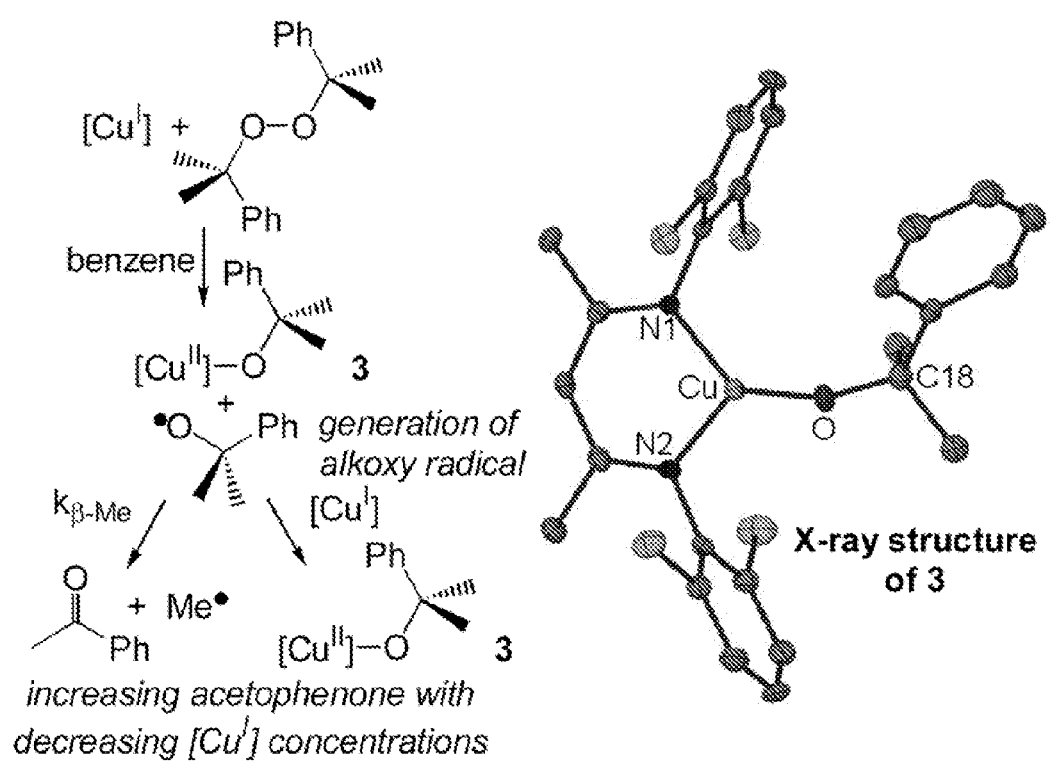
FIG. 8 is a scheme showing the generation and capture of the .OCMe$_2$Ph radical by $[Cu^I]$; and an X-ray structure of intermediate 3.
Figure 9:
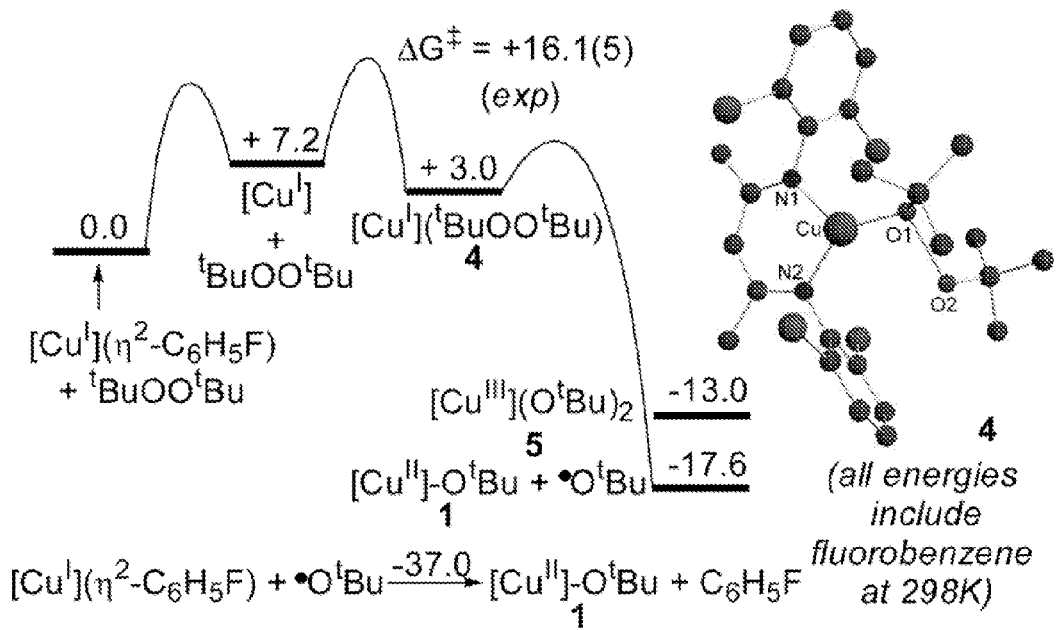
FIG. 9 shows the DFT energies of various putative intermediates; and the structure of 4.

The reaction of [Cu$^I$] with dicumyl peroxide provides further evidence for the formation of alkoxy radicals RO. in the reaction between [Cu$^I$] and dialkyl peroxides ROOR. Facile unimolecular decomposition of the cumyloxyl radical PhMe$_2$CO. to acetophenone and a methyl radical (k=3.7(5)× 10$^5$ s$^{-1}$ in benzene at 30° C.; FIG. 8) provides a convenient probe for the presence of alkoxy radicals. Reaction of {[Cl$_2$NN]Cu}2(benzene) with 4 equiv of dicumyl peroxide in fluorobenzene at room temperature allows for the isolation of [CuI]—OCMe2Ph (3) as red crystals of 3.½(dicumyl peroxide) from pentane. The structure of 3 shows a slightly distorted trigonal planar geometry with N1-Cu—O1 and N2-Cu—O1 angles of 134.50(9)° and 129.02(10)° along with a short Cu—O bond length of 1.788(2) Å. These values are very similar to those found in the structure of previously reported 1 (134.04(9)°, 129.64(9)°, and 1.785(2) Å, respectively). In fluorobenzene, 3 exhibits closely related optical absorption (λ$_{max}$=467 nm, ε8=3760 M$^{-1}$ cm$^{-1}$) and EPR spectra. The reaction between [Cu$^I$] (initially 0.50 mM) and 20 equiv of dicumyl peroxide in fluorobenzene at 10° C. gives 3 under pseudo-first-order kinetics with an overall second-order rate constant k=0.79(5) M$^{-1}$ s$^{-1}$. This is about three times slower compared to the analogous reaction with tBuOOtBu, reflecting the added steric bulk of dicumyl peroxide vs di-tert-butyl peroxide. Reaction of [Cu$^I$] and dicumyl peroxide in a 1:2 molar ratio at rt in benzene-d$_6$ reveals that acetophenone forms, suggesting the intermediacy of the PhMe$_2$CO. radical (FIG. 8). Notably, the amount of acetophenone formed decreases with increasing initial [Cu$^I$] concentration, indicating more efficient trapping of the PhMe$_2$CO. radical at higher [Cu$^I$] concentrations. For instance, with an initial [Cu$^I$] concentration of 0.01 M, acetophenone is produced in 71(2)% yield whereas an initial [Cu$^I$] concentration of 0.04 M gives a 26(2)% yield of acetophenone. Based on these data and the rate of β-Me scission for PhMe$_2$CO., we can crudely estimate the rate of bimolecular trapping of the cumyloxyl radical by [Cu$^I$] in benzene at rt to be on the order of 2×10$^7$ M$^{-1}$ s$^{-1}$. We employed theory to provide deeper insight into the reaction between [Cu$^I$] and tBuOOtBu. Binding of fluorobenzene (η$^2$-CC) and pyridine (κ$^1$-N) to the naked, two-coordinate [Cu$^I$] fragment is exergonic by 7.2 and 16.7 kcal/mol, respectively. DFT calculations of the putative intermediate [Cu$^I$](tBuOOtBu) (4) reveal a minimum that is 3.0 kcal/mol higher in free energy than the [Cu$^I$](η$^2$-C$_6$H$_5$F) species. Loss of tBuO. from adduct 4 to give [Cu$^{II}$]-OtBu (1)+tBuO. is calculated to result in a $\Delta G_{rxn}$ (298 K) of −20.6 kcal/mol (FIG. 9).

A diamagnetic square planar copper(III) bis(tert-butoxide) complex [Cu$^{III}$](OtBu)$_2$ (5) representing the formal oxidative addition of tBuOOtBu to [Cu$^I$] was also found via simulation. Although 5 is considerably lower in free energy than the adduct 4 by 17 kcal/mol, species 5 nonetheless is predicted to be unstable by 4.6 kcal/mol in free energy toward loss of the tBuO. radical to give 1. The endothermic (ΔH=+15.0 kcal/mol) fragmentation 5→1+tBuO. is strongly entropically driven (−TΔS=−19.6 kcal/mol at 298 K). Addition of tBuO. to [Cu$^I$](η$^2$-C$_6$H$_5$F) to give 1+fluorobenzene is extremely exergonic with a calculated $\Delta G_{rxn}$ of −37.0 kcal/mol. Thus, the tBuO. radical formed in the reaction of [Cu$^I$] with tBuOOtBu is likely to be rapidly captured by another equivalent of [Cu$^I$].

Based on experimental and theoretical considerations, we propose that the rate-determining step in the reaction of tBuOOtBu with [Cu$^I$] is the generation of the peroxide adduct [Cu$^I$](tBuOOtBu) (4, FIGS. 7 and 9) from a [Cu$^I$](L) species (L=η$^2$-fluorobenzene or pyridine). This peroxide adduct 4 is primed for loss of the tBuO. radical. While we have been unable to find a transition state for the loss of tBuO. from 4, potential energy scans indicate that further lengthening of the O—O bond in 4 and a Cu—O bond in 5 result in flat potential energy surfaces for the conversion of 4 to 5 (or 1+tBuO.) and the dissociation of tBuO. from 5, respectively. The large drop in free energy associated with the loss of tBuO. from 4 and the correlation between lower reaction rates in the presence of pyridine strongly suggest that the rate-determining step in the formation of 1 from the [Cu$^I$](L) species and tBuOOtBu corresponds to competition between tBuOOtBu and L for coordination to the [Cu$^I$] fragment (FIG. 7(a)).

These results point to the kinetically facile and thermodynamically favorable generation of alkoxy radicals by the [Cu$^I$]/tBuOOtBu system, suggesting that tBuO. may participate in HAA in C—H functionalization catalysis. Second-order rate constants for HAA reactions of benzylic and unactivated sp$^3$ C—H substrates R—H by tBuO. at rt span ca. 10$^{6-8}$ M$^{-1}$ s$^{-1}$ (equation 1), comparable to our estimate for trapping of PhMe$_2$CO. by [Cu$^I$] (equation 2). Low concentrations of [Cu$^I$] present in catalytic C—H functionalization reactions (~1 mM), however, may bias the tBuO. radical toward productive HAA with R—H to give R. vs. capture by [Cu$^I$] to give 1.

(1)

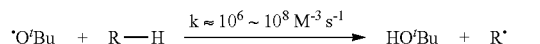

(2)

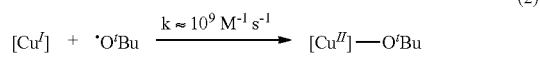

Figure 10:
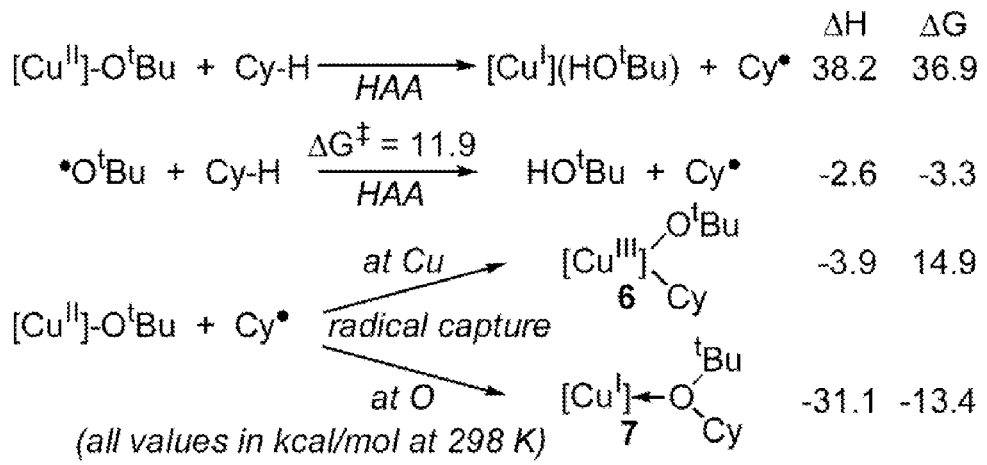
FIG. 10 is a scheme showing various putative intermediates and their corresponding calculated ΔH and ΔG values.

To illustrate the potential for the tBuO. radical generated upon reaction of [Cu$^I$] with tBuOOtBu to engage in HAA of a substrate R—H, we employed cyclohexane as a solvent and substrate which undergoes facile HAA by tBuO. (k=8.1×10$^5$ M$^{-1}$ s$^{-1}$ in a 2:1 tBuOOtBu/benzene mixture at 25° C.). Reaction of [Cu$^I$] (6.7 mM) with tBuOOtBu (10 equiv) in cyclohexane at rt for 24 h gave a 50% yield of the ether Cy-OtBu. Extending the reaction time to 72 h increased the yield to 60% employing only 5 mol % [Cu$^I$] (3.3 mM). The observation of the C—H functionalized product suggests that the tBuO. radical generated upon reaction of tBuOOtBu with [Cu$^I$] abstracts a H-atom from the strong C—H bond of cyclohexane (C—H BDE≈97 kcal/mol) to give the cyclohexyl radical Cy. Control experiments reveal that the copper(II) alkoxide 1 does not engage in HAA with cyclohexane (Cy-H) under these conditions. After 17 h at rt in cyclohexane, very little decay (3.5%) of 1 occurs Akin to the Kharasch-Sosnovsky reaction with peroxyesters, we hypothesize that C—O bond formation results from capture of the Cy. radical by the [Cu$^{II}$]-OtBu intermediate (FIG. 10). Since the tBuO. radical undergoes unimolecular β-scission with k=2.0(4)×10$^4$ s$^{-1}$ in benzene at 25° C., it is unlikely that a significant amount of Cy-OtBu results from the direct coupling of highly reactive Cy. and tBuO. radicals present in minute concentrations in solution.

We employed theory to examine this reaction in detail. Consistent with experiment, HAA of Cy-H by [Cu$^{II}$]-OtBu is very disfavored (ΔG(298 K)=36.9 kcal/mol) and not expected to occur under mild conditions. In contrast, HAA of Cy-H by tBuO. is calculated to proceed with a low activation barrier ΔG‡ (298 K)=11.9 kcal/mol (exp=9.4(7) kcal/mol) and is thermodynamically favored due to the high tBuO—H bond strength. We then considered the thermodynamics of two possible pathways for the formation of the Cy-OtBu bond via capture of Cy. by [Cu$^{II}$]-OtBu. Direct addition to the Cu center to give the square planar copper(III) organometallic [Cu$^{III}$](Cy)(OtBu) (6) is enthalpically favorable (ΔH=−3.9 kcal/mol), but entropically unfavorable (ΔS=63.1 e.u.) leading to an overall endergonic transformation (ΔG(298 K)=+14.9 kcal/mol). On the other hand, direct capture of Cy. at the O-atom of 3 to form the copper(I) ether adduct [Cu$^I$](O(Cy)tBu) (7) is thermodynamically favorable with ΔG(298 K)=−13.4 kcal/mol. As a result, C—O reductive elimination from putative 6 to form the product ether Cy-OtBu bound to [Cu$^I$] is highly favored (ΔG(298 K)=−28.3 kcal/mol).

The ability of low concentrations of [Cu$^I$] (e.g., 1 mM) to generate the highly potent radical tBuO. at rates ca. 10$^9$ faster than the uncatalyzed thermal homolytic cleavage of tBuOOtBu at rt opens the possibility of efficient HAA reactions with substrates R—H containing unactivated sp$^3$-hybridized C—H bonds under mild conditions. Importantly, the [Cu$^{II}$]-OtBu species formed alongside the tBuO. radical is capable of capturing the C-centered radical Cy. to form a new C—O bond in Cy-OtBu. In contrast to the common use of peroxyesters RC(O)OOtBu with allylic substrates to give the corresponding allylic carboxylates, catalytic ether formation at sp$^3$ C—H bonds with organoperoxides is rare. Moreover, facile acid-base chemistry available to the [Cu$^{II}$]-OtBu intermediate 1 with substrates H-FG such as amines H—NR$^1$R$^2$ to form copper amides [Cu]-NR$^1$R$^2$ may allow for the development of a family of sp$^3$ C—H functionalization protocols that deliver products R-FG in new variations of the Kharasch-Sosnovsky reaction.

Example 25

Synthesis of [Cl$_2$NN]Cu(py) (2)

In a glovebox, pyridine (200.0 μL, 2.473 mmol) was added into a stirring slurry of {[Cl$_2$NN]Cu}$_2$(benzene) (0.567 g, 0.579 mmol) in ether (15 mL), resulting to a yellow-orange mixture. After stirring overnight, the mixture was passed through a Celite® filter stick and evaporated to dryness. The residue was washed with ether (~3 mL) and dried in vacuo to afford 0.462 g (75%) of bright yellow crystals. A saturated ether solution (~2 mL) of the adduct with a few drops of added pyridine was layered with pentane (~1 mL) and allowed to stand overnight at −35° C. Very bright yellow crystals formed that were suitable for X-ray diffraction. $^1$H NMR (400 MHz, benzene-d$_6$): δ 8.01 (d, 2, o-H of py ring), 7.04 (d, 3, m-H of Ph ring), 6.56 (t, 1, p-H of py ring), 6.34 (t, 2, p-H of Ph ring), 6.22 (t, 2, m-H of py ring), 5.03 (s, 1, backbone-CH), 1.87 (s, 6, backbone-CH$_3$); $^{13}$C {$^1$H} NMR (benzene-d$_6$): δ 164.39, 149.89, 148.71, 135.84, 130.85, 128.72 (overlaps with solvent peak), 124.89, 123.31, 95.45, 23.85. Anal. Calcd. For C$_{22}$H$_{18}$Cl$_4$N$_3$Cu: C, 49.88; H, 3.42; N, 7.93. Found: C, 47.76; H, 3.37; N, 7.53.

Example 26

Synthesis of [Cl$_2$NN]Cu—OCMe$_2$Ph (3)

To a stirring slurry of {[Cl$_2$NN]Cu}$_2$(benzene) (0.281 g, 0.291 mmol) in ca. 5 mL fluorobenzene at RT was added 4 equivalents of dicumyl peroxide (0.292 g, 1.08 mmol). After 20 minutes of stirring the solution turned dark red. All volatiles were removed in vacuo and the resulting residue was dissolved in ca. 5 mL pentane. The solution was passed through Celite® and separated into 3 vials. The dark red solutions were allowed to stand at −40° C. overnight. While most of the solids thus obtained were powdery, a few deep red crystals formed that were suitable for X-ray diffraction. In the unit cell of this substance, ½ equiv. DCP is present and was used in the calculation of its formula for elemental analysis. Anal. Calcd for C$_{35}$H$_{35}$Cl$_4$N$_2$O$_2$Cu.½ (dicumyl peroxide): C, 58.30; H, 4.89; N, 3.89. Found: C, 58.54; H, 4.86; N, 3.79.

INCORPORATION BY REFERENCE

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicant reserves the right to physically incorporate into this application any and all materials and information from any such articles, patents, patent applications, or other physical and electronic documents.

EQUIVALENTS

The invention has been described broadly and generically herein. Those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention. Further, each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

We claim:
1. A method of forming an ether, comprising:
  combining a substrate comprising a reactive C—H bond, an alcohol, a peroxide, and a copper-containing catalyst, thereby forming an ether;
wherein:
the substrate comprising the reactive C—H bond is represented by:

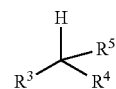

wherein:
R$^3$ is alkyl, alkenyl, alkynyl, aryl, heteroaryl, aralkyl, heteroaralkyl, carbocyclyl, heterocyclyl, polycyclyl, carbonyl, ester or ether;
R$^4$ is hydrogen, alkyl, alkenyl, alkynyl, aryl, heteroaryl, aralkyl, heteroaralkyl, carbocyclyl, heterocyclyl, polycyclyl, carbonyl, ester or ether; or R$^3$ and R$^4$ taken together are oxo;
R$^5$ is hydrogen, alkyl, alkenyl, alkynyl, aryl, heteroaryl, aralkyl, heteroaralkyl, carbocyclyl, heterocyclyl, polycyclyl, carbonyl, ester or ether; and
the substrate is optionally substituted with 1-3 substituents selected from the group consisting of halogen, alkyl, alkenyl, alkynyl, hydroxyl, amino, nitro, amide, phosphonate, carboxyl, silyl, ether, sulfonyl, ester, fluoroalkyl, trifluoromethyl, and cyano; and
the copper-containing catalyst is represented by Formula I or an enantiomer, stereoisomer or diastereomer thereof:

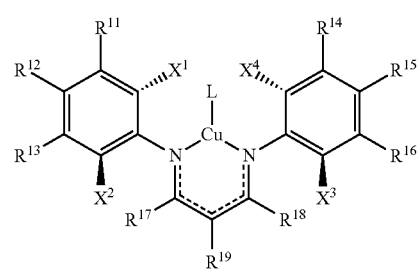

wherein:

$R^{11}$ to $R^{19}$ are independently selected from the group consisting of hydrogen, alkyl, aryl, aralkyl, halogen, cyano, nitro and trifluoromethyl;

$X^1$ to $X^4$ are independently selected from the group consisting of hydrogen, halogen, alkyl, perhaloalkyl, and aryl; and L is absent or a Lewis base.

2. The method of claim 1, wherein the alcohol is an aliphatic alcohol.

3. The method of claim 1, wherein the peroxide is tert-butyl peroxide.

4. The method of claim 1, wherein $R^{17}$-$R^{19}$ represent independently for each occurrence hydrogen, methyl, trifluoromethyl, phenyl, or tert-butyl.

5. The method of claim 1, wherein $R^{17}$ and $R^{18}$ represent tert-butyl.

6. The method of claim 1, wherein $R^{17}$ and $R^{18}$ represent trifluoromethyl.

7. The method of claim 1, wherein $R^{19}$ is hydrogen.

8. The method of claim 1, wherein $X^1$ to $X^4$ are independently for each occurrence halogen or perfluoroalkyl.

9. The method of claim 8, wherein $X^1$ to $X^4$ are independently for each occurrence Cl, I, Br, or $CF_3$.

10. The method of claim 9, wherein $X^1$ to $X^4$ are Cl.

11. The method of claim 9, wherein $X^1$ to $X^4$ are $CF_3$.

12. The method of claim 1, wherein L is aromatic.

13. The method of claim 12, wherein L is benzene.

14. The method of claim 1, wherein the copper-containing catalyst is selected from the group consisting of:

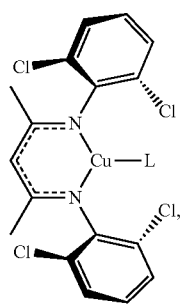
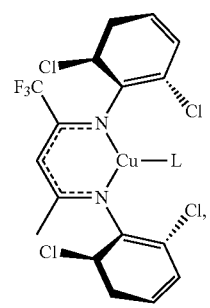
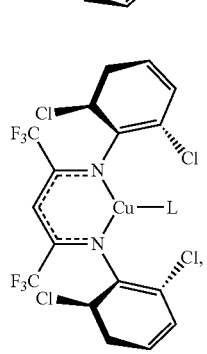
and
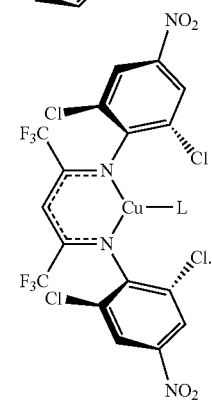

15. The method of claim 1, wherein the copper-containing catalyst is:

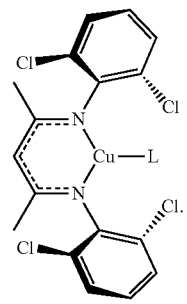

16. The method of claim 1, wherein the copper-containing catalyst is:

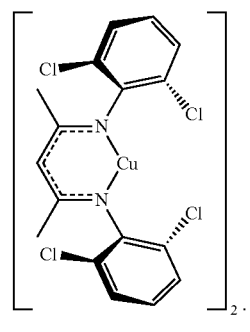

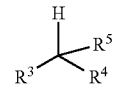
(benzene)

17. A method of forming an ether, comprising:

combining a substrate comprising a reactive C—H bond, an aryl acetate, a peroxide, and a copper-containing catalyst, thereby forming an ether;

wherein:

the substrate comprising the reactive C—H bond is represented by:

$$R^3\underset{R^4}{\overset{H}{-}}R^5$$

wherein:

$R^3$ is alkyl, alkenyl, alkynyl, aryl, heteroaryl, aralkyl, heteroaralkyl, carbocyclyl, heterocyclyl, polycyclyl, carbonyl, ester or ether;

$R^4$ is hydrogen, alkyl, alkenyl, alkynyl, aryl, heteroaryl, aralkyl, heteroaralkyl, carbocyclyl, heterocyclyl, polycyclyl, carbonyl, ester or ether; or $R^3$ and $R^4$ taken together are oxo;

$R^5$ is hydrogen, alkyl, alkenyl, alkynyl, aryl, heteroaryl, aralkyl, heteroaralkyl, carbocyclyl, heterocyclyl, polycyclyl, carbonyl, ester or ether; and the substrate is optionally substituted with 1-3 substituents selected from the group consisting of halogen, alkyl, alkenyl, alkynyl, hydroxyl, amino, nitro, amide, phosphonate, carboxyl, silyl, ether, sulfonyl, ester, fluoroalkyl, trifluoromethyl, and cyano; and the copper-containing catalyst is represented by Formula I or an enantiomer, stereoisomer or diastereomer thereof:

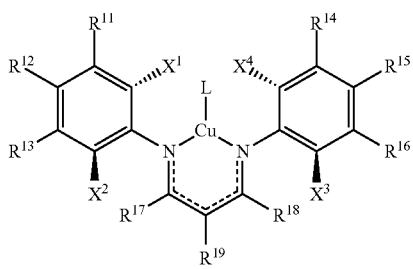

wherein:
R¹¹ to R¹⁹ are independently selected from the group consisting of hydrogen, alkyl, aryl, aralkyl, halogen, cyano, nitro and trifluoromethyl;
X¹ to X⁴ are independently selected from the group consisting of hydrogen, halogen, alkyl, perhaloalkyl, and aryl; and
L is absent or a Lewis base.

18. A method of forming a thioether, comprising
combining a substrate comprising a reactive C—H bond, an acetyl-protected thiol, a peroxide, and a copper-containing catalyst, thereby forming a thioether;
wherein:
the substrate comprising the reactive C—H bond is represented by:

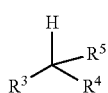

wherein:
R³ is alkyl, alkenyl, alkynyl, aryl, heteroaryl, aralkyl, heteroaralkyl, carbocyclyl, heterocyclyl, polycyclyl, carbonyl, ester or ether;
R⁴ is hydrogen, alkyl, alkenyl, alkynyl, aryl, heteroaryl, aralkyl, heteroaralkyl, carbocyclyl, heterocyclyl, polycyclyl, carbonyl, ester or ether; or R³ and R⁴ taken together are oxo;
R⁵ is hydrogen, alkyl, alkenyl, alkynyl, aryl, heteroaryl, aralkyl, heteroaralkyl, carbocyclyl, heterocyclyl, polycyclyl, carbonyl, ester or ether; and the substrate is optionally substituted with 1-3 substituents selected from the group consisting of halogen, alkyl, alkenyl, alkynyl, hydroxyl, amino, nitro, amide, phosphonate, carboxyl, silyl, ether, sulfonyl, ester, fluoroalkyl, trifluoromethyl, and cyano; and
the copper-containing catalyst is represented by Formula I or an enantiomer, stereoisomer or diastereomer thereof:

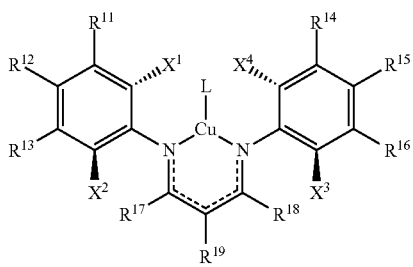

wherein:
R¹¹ to R¹⁹ are independently selected from the group consisting of hydrogen, alkyl, aryl, aralkyl, halogen, cyano, nitro and trifluoromethyl;
X¹ to X⁴ are independently selected from the group consisting of hydrogen, halogen, alkyl, perhaloalkyl, and aryl; and
L is absent or a Lewis base.

19. A method of forming a thioether, comprising
combining a substrate comprising a reactive C—H bond, a disulfide, a peroxide, and a copper-containing catalyst, thereby forming a thioether;
wherein:
the substrate comprising the reactive C—H bond is represented by:

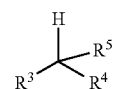

wherein:
R³ is alkyl, alkenyl, alkynyl, aryl, heteroaryl, aralkyl, heteroaralkyl, carbocyclyl, heterocyclyl, polycyclyl, carbonyl, ester or ether;
R⁴ is hydrogen, alkyl, alkenyl, alkynyl, aryl, heteroaryl, aralkyl, heteroaralkyl, carbocyclyl, heterocyclyl, polycyclyl, carbonyl, ester or ether; or R³ and R⁴ taken together are oxo;
R⁵ is hydrogen, alkyl, alkenyl, alkynyl, aryl, heteroaryl, aralkyl, heteroaralkyl, carbocyclyl, heterocyclyl, polycyclyl, carbonyl, ester or ether; and
the substrate is optionally substituted with 1-3 substituents selected from the group consisting of halogen, alkyl, alkenyl, alkynyl, hydroxyl, amino, nitro, amide, phosphonate, carboxyl, silyl, ether, sulfonyl, ester, fluoroalkyl, trifluoromethyl, and cyano; and
the copper-containing catalyst is represented by Formula I or an enantiomer, stereoisomer or diastereomer thereof:

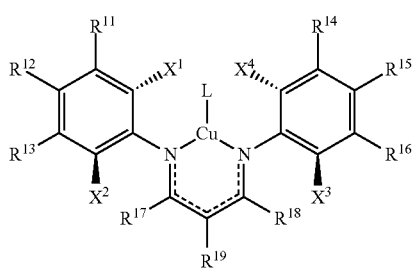

wherein:
R¹¹ to R¹⁹ are independently selected from the group consisting of hydrogen, alkyl, aryl, aralkyl, halogen, cyano, nitro and trifluoromethyl;
X¹ to X⁴ are independently selected from the group consisting of hydrogen, halogen, alkyl, perhaloalkyl, and aryl; and
L is absent or a Lewis base.

20. The method of claim 17, wherein the peroxide is tert-butyl peroxide.

21. The method of claim 18, wherein the peroxide is tert-butyl peroxide.

22. The method of claim 19, wherein the peroxide is tert-butyl peroxide.

* * * * *